United States Patent
Fukui et al.

(10) Patent No.: US 9,169,231 B2
(45) Date of Patent: Oct. 27, 2015

(54) ANTI-OBESITY AGENT COMPRISING COMPOUND CONTAINING BENZOTROPOLONE RING

(71) Applicant: SUNTORY HOLDINGS LIMITED, Osaka (JP)

(72) Inventors: Yuko Fukui, Mishima-gun (JP); Sumio Asami, Mishima-gun (JP); Mitsuru Maeda, Mishima-gun (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 0 days.

(21) Appl. No.: 14/517,956

(22) Filed: Oct. 20, 2014

(65) Prior Publication Data

US 2015/0038573 A1    Feb. 5, 2015

Related U.S. Application Data

(60) Continuation of application No. 14/150,461, filed on Jan. 8, 2014, now abandoned, which is a division of application No. 13/321,299, filed as application No. PCT/JP2010/058624 on May 21, 2010, now Pat. No. 8,658,237.

(30) Foreign Application Priority Data

May 21, 2009   (JP) .................................. 2009-123585

(51) Int. Cl.
| | |
|---|---|
| *C07D 311/62* | (2006.01) |
| *A61K 31/352* | (2006.01) |
| *C07D 311/64* | (2006.01) |
| *A23L 1/30* | (2006.01) |
| *A61K 31/122* | (2006.01) |
| *A61K 31/353* | (2006.01) |
| *C07D 311/04* | (2006.01) |
| *A23F 3/16* | (2006.01) |
| *A23L 2/52* | (2006.01) |
| *C07C 62/38* | (2006.01) |

(52) U.S. Cl.
CPC ............... *C07D 311/64* (2013.01); *A23F 3/16* (2013.01); *A23L 1/3002* (2013.01); *A23L 2/52* (2013.01); *A61K 31/122* (2013.01); *A61K 31/353* (2013.01); *C07C 62/38* (2013.01); *C07D 311/04* (2013.01); *C07D 311/62* (2013.01); *A23V 2002/00* (2013.01)

(58) Field of Classification Search
CPC ............................ C07D 311/62; A61K 31/352
See application file for complete search history.

(56) References Cited

U.S. PATENT DOCUMENTS

| 2005/0049284 A1 | 3/2005 | Ho et al. |
| 2010/0150895 A1 | 6/2010 | Mazzio et al. |

FOREIGN PATENT DOCUMENTS

| JP | 2004155784 A | 6/2004 |
| JP | 2006052191 A | 2/2006 |
| JP | 2007504168 A | 3/2007 |
| JP | 2009028010 A | 2/2009 |
| WO | WO-9922728 A1 | 5/1999 |
| WO | WO-2005021479 A1 | 3/2005 |
| WO | WO2006004114 A | 1/2006 |
| WO | WO-2007141945 A1 | 12/2007 |

OTHER PUBLICATIONS

International Search Report mailed Jun. 22, 2010 issued in PCT/JP2010/058624.
Supplementary European Search Report mailed Oct. 1, 2012 issued in EP Application No. 10777827.6.
Sang et al., New dibenzotropolone derivatives characterized from black tea using LC/MS/MS, Bioorganic & Medicinal Chemistry, Jun. 1, 2004, vol. 12, No. 11, pp. 3009-3017.
Zheng et al., "Construction of a three-dimensional pharmacophore for Bcl-2 inhibitors by flexible docking and the multiple copy simultaneous search method", Bioorganic & Medicinal Chemistry, Aug. 10, 2007, vol. 15, No. 19, pp. 6407-6417.
Sang et al., "Enzymatic synthesis of tea theaflavin derivatives and their anti-inflammatory and cytotoxic activities", Bioorganic & Medicinal Chemistry, Jan. 1, 2004, vol. 12, pp. 459-467.
Clinical Guidelines on the Identification, Evaluation, and Treatment of Overweight and Obesity in Adults, http://www.nhlbi.nih.gov/guidlines/obesity/ob_gllns.pdf, accessed on Feb. 20, 2013.

*Primary Examiner* — Rebecca Anderson
*Assistant Examiner* — Karen Cheng
(74) *Attorney, Agent, or Firm* — Drinker Biddle & Reath LLP

(57) ABSTRACT

The object of the present invention is to provide an anti-obesity agent which contains a tea-derived component and which is safe and does not compromise the flavor of foods and beverages.
According to the present invention, a safe and palatable anti-obesity agent can be provided by incorporating a benzotropolone ring-containing compound which has tea-derived, high inhibitory activities against lipase and alfa-glucosidase. The anti-obesity agent of the present invention does not compromise the flavor of foods and beverage, has palatability, and can be used in various use applications including foods and beverages intended for health enhancement such as reduction in triglycerides.

12 Claims, 2 Drawing Sheets

ANTI-OBESITY AGENT COMPRISING COMPOUND CONTAINING BENZOTROPOLONE RING

CROSS REFERENCE TO RELATED APPLICATIONS

This is a continuation application of co-pending prior application Ser. No. 14/150,461 filed Jan. 8, 2014, which is a divisional application of prior application Ser. No. 13/321,299 (now U.S. Pat. No. 8,658,237 issued Feb. 25, 2014) having a §371 date of Nov. 18, 2011, which is a national stage filing based on PCT International Application PCT/JP2010/058624 filed on May 21, 2010, and claims benefit of Japanese Application No. 2009-123585 filed May 21, 2009. Which are herein incorporated by reference in their entirety.

TECHNICAL FIELD

The present invention relates to an anti-obesity agent containing a benzotropolone ring-containing compound.

BACKGROUND ART

Obesity is one of the most significant diseases in modern society and the main factor of obesity is excessive intake of fat. Excessive intake of fat is known to cause not only obesity but also diabetes, hyperlipidemia, hypertension, arteriosclerosis, and the like that are attributable to obesity. The condition in which two or more of hyperglycemia, hypertension, and hyperlipidemia develop with visceral fat obesity is called metabolic syndrome (visceral fat syndrome), which is at high risk of causing cardiac diseases and stroke and thus has been regarded as a problem in recent years. As a therapeutic agent for obesity, for example, Xenical®, which has a suppressive action on fat absorption from the gastrointestinal tract due to its lipase inhibitory activity, is commercially available as an anti-obesity agent; however, its side effects such as steatorrhea, increased frequency of defecation, loose stool, diarrhea, and stomachache have been reported and the agent thus cannot be necessarily safe (Non-Patent Document 1).

In order to prevent obesity, cutting calories on a restrictive diet is an effective way. Nevertheless, it is often hard to practice it in daily life because substantial nutritional guidance has to be received. Accordingly, suppressing in a safe and healthy manner the absorption of diet-derived fat into the body is expected to be a realistic and effective measure for treatment of obesity and obesity-related diseases or health enhancement.

Under these circumstances, the development of specified health foods that are safe and proven effective in humans is attracting attention. To date, the following food materials which suppress the elevation of serum triglyceride level after meals are commercially marketed as specified health foods: globin digest which suppresses fat absorption by its pancreatic lipase inhibition; diacylglycerol, which has digestive and absorptive properties different from triacylglycerol; eicosapentaenoic acid (EPA) and docosahexaenoic acid (DHA), which are purified from fish oil; and the like.

Also, recent interest is focusing on plant-derived lipase inhibiting active substances, and particularly, the following polyphenols which have lipase inhibitory activity have been reported: plant bark-derived tannin; tannins and flavonoids and glycosides thereof in the legume Cassia nomame; lipid absorption-inhibiting foods containing epigallocatechin gallate and epicatechin gallate, which are main components in green tea; lipase inhibitors comprising water extracts from pepper, shimeji mushroom, pumpkin, maitake mushroom, seaweed Hizikia fusiformis, green tea, oolong tea, and the like; flavones and flavonols; hydroxybenzoic acids (gallic acid), triterpene compounds and derivatives thereof; anti-obesity agents containing, as an active ingredient, procyanidin from tamarind; and the like. Further known are lipase inhibitory action of grape seed extract (Non-Patent Document 2); lipase inhibitory action from Salacia reticulate-derived polyphenol, and anti-obesity action in rats (Non-Patent Document 3); oolong tea extract-derived anti-obesity action in mice (Non-Patent Document 4); and the like. In addition, teas contain a lot of catechins, many components of which have been separated and identified (Non-Patent Document 5), and there are reports on lipase inhibitors containing tea-derived components (Patent Documents 1 and 2). Above all, theaflavins, known as pigments of black tea and oolong tea, exhibit strong lipase inhibitory activity in proportion to the number of gallate groups in a molecule (Patent Document 2, Non-Patent Document 6). However, the content and proportion of these theaflavins are not constant among teas.

Alfa-glucosidase inhibiting substances have an inhibitory action on the elevation of blood glucose level by inhibiting alfa-glucosidase, which is localized on small intestinal epithelium, and by suppressing or delaying the decomposition and absorption of sugar. Accordingly, alfa-glucosidase-inhibiting substances are useful in various diseases such as diabetes and obesity, which are derived from the chronicity of high blood sugar symptoms.

Since alfa-glucosidase inhibitory activity was discovered in malt component in 1933, many alfa-glucosidase-inhibiting substances that are derived from wheat and pulse have been discovered. In 1966, nojirimycin, which has alfa-glucosidase inhibitory activity, was isolated from a microbial metabolite and its structure was determined. From mulberry leaf extract, a related compound of nojirimycin, 1-deoxynojirimycin, was obtained, which is known to have alfa-glucosidase inhibitory activity, and a method of extraction for keeping the activity from decreasing is disclosed (Patent Document 3).

A compound that contains a 13-membered ring cyclitol structure having a sulfoxide, which is isolated from the extract of the root of Salacia reticulate, is reported to have maltase inhibitory activity (Patent Document 4). Diacylated pelargonidin, cyanidin, and peonidin 3-sophoroside-5-glucosides are reported to have maltase inhibitory activity as an anthocyanin compound isolated from morning glories or the root of purple sweet potato (Non-Patent Document 7). The maltase inhibitory activity has also been confirmed in the components contained in tea leaves, such as theasinensin A, theaflavin derivatives having a galloyl group, and proanthocyanidins having epiafzelechingallate as a constitutional unit. Although theaflavin derivatives having a galloyl group have maltase inhibitory activity, they are contained in tea leaves in only a small proportion, 0.1 to 0.2% (Patent Document 5, Non-Patent Document 8).

Black tea theaflavins and green tea catechins are reported to have alfa-glucosidase inhibitory activity (Non-Patent Document 8); the activity has been confirmed in catechins having a galloyl group at their 3 position including epigallocatechin-3-O-gallate (hereinafter referred to as "EGCG") and epicatechin-3-O-gallate, and theaflavins including theaflavin-3-O-gallate and theaflavin-3,3'-di-O-gallate. The fractions and the like of black tea have also been examined for their alfa-glucosidase inhibitory activity; polymeric fractions formed by fermentation are also known to have the activity (Non-Patent Document 9).

On the other hand, it is known that in fermentation process in production of black tea or oolong tea, polyphenols such as catechins or gallic acid are condensed into a compound having a benzotropolone ring through the activity of enzymes such as polyphenol oxidase in tea leaves (Non-Patent Document 10).

It is reported that aside from theaflavins, many benzotropolone ring-containing compounds are present in teas. Reported are, for example, apoptosis induction caused by purpurogallin derivatives (Patent Document 6) and a method of manufacturing epitheaflagallins for use in foods (Patent Document 7), an enzymatic method of manufacturing a theaflavin type trimer, theadibenzotropolone A, and presence thereof in black tea (Non-Patent Document 11), and the like. The anti-inflammatory actions of various benzotropolone ring-containing compounds (Non-Patent Document 12) are also known. Nevertheless, for benzotropolone ring-containing compounds other than theaflavins and epitheaflagallins, nothing is known about their lipase inhibitory action relating to fat absorption and their alfa-glucosidase inhibitory action relating to their inhibitory action on the elevation of blood glucose level.

CITATION LIST

Patent Document

Patent Document 1: WO2005/077384
Patent Document 2: WO 2006/004110
Patent Document 3: Japanese Patent Public Disclosure 2007-60908
Patent Document 4: Japanese Patent Public Disclosure 2008-137925
Patent Document 5: Japanese Patent Public Disclosure 2007-231009
Patent Document 6: Japanese Patent Public Disclosure 2004-359576
Patent Document 7: WO 2007-141945

Non-Patent Document

Non-Patent Document 1: Lancet 1998; 352: 167-172
Non-Patent Document 2: Nutrition 2003; 19(10): 876-879
Non-Patent Document 3: J. Nutr. 2002; 132: 1819-1824
Non-Patent Document 4: Int. J. Obes. 1999; 23: 98-105
Non-Patent Document 5: Journal of the Japanese Society for Food Science and Technology, Vol. 46, No. 3, pp. 138-147, March 1999
Non-Patent Document 6: Chem. Pharm. Bull. 2008; 56: 266-272
Non-Patent Document 7: J. Agric. Food Chem. 2001, 49, 1952-1956
Non-Patent Document 8: J. Agric. Food. Chem., 55, 99-105, 2007
Non-Patent Document 9: Chem. Pharm. Bull. 56(3), 266-272, 2008
Non-Patent Document 10: Tetrahedron 1973; 29: 125-142
Non-Patent Document 11: Tetrahedron Letters 2002; 43: 7129-7133
Non-Patent Document 12: Bioorganic & Medicinal Chemistry 2004; 12: 459-467

SUMMARY OF THE INVENTION

Technical Problem

Even if some effect is found to be obtained from a plant extract, unless the quantity of the active components contained in the extract is determined, it is difficult to ensure stable maintenance of its anti-obesity activity because the extract is of natural product origin. Further, some of the reported lipase inhibitors and alfa-glucosidase inhibitors as shown above are not sufficiently effective.

A less palatable, vegetable-derived anti-obesity agent, when used as foods or beverages, is expected to make a negative influence on their flavor. On the other hand, a more palatable, tea-derived anti-obesity agent can possibly be an effective material candidate; however, for example, even when we drink palatable black tea or oolong tea in order to lower lipid, we cannot obtain its effect without drinking the tea in large amounts, and thus to practice it in daily life is thus not realistic. Simply condensed black tea or oolong tea is also not appropriate to drink as a realistic measure because of its strong bitterness and astringency and increased caffeine.

Accordingly, an object of the present invention is to provide an anti-obesity agent which is of natural product origin and effective.

Another object of the present invention is to provide a tea-derived, palatable inhibitor of lipase activity which shows a highly inhibitory activity against pancreatic lipase and suppresses absorption of diet-derived fat, and/or contributes to suppression and prevention of obesity. Still another object is to provide an alfa-glucosidase inhibitor which suppresses absorption of diet-derived sugar and contributes to long-term prevention and/or treatment of diabetes resulting from the chronicity of high blood sugar symptoms.

Still another object of the present invention is to provide foods and beverages which are palatable and intended to lower blood triglyceride and which enhance health.

Still another object of the present invention is to provide a pharmaceutical composition which suppresses absorption of diet-derived fat and elevation of blood triglyceride.

Solution to Problem

As a result of intensive studies to solve the above problems, the present inventors have found a component from tea leaves which potently inhibits pancreatic lipase, essential for fat absorption, and which has high alfa-glucosidase inhibitory activity. Specifically, the inventors have assayed the inhibitory activities of various polyphenols present in tea leaves against lipase and alfa-glucosidase, and found out that the benzotropolone ring-containing compounds of Formula (1) have strong lipase inhibitory activity and strong alfa-glucosidase inhibitory activity. These compounds are oxides of catechins and polyphenols which are contained in black tea, and thus are superior in flavor and safety and can be taken for long periods of time. From these findings, the inventors have found that it is possible to provide foods and beverages, to which a lipase inhibitor and an alfa-glucosidase inhibitor are added, which are intended to suppress absorption of diet-derived fat and sugar and elevation of blood triglyceride and to prevent and/or treat diabetes resulting from the chronicity of high blood sugar symptoms is in the long run. The present invention has been thus accomplished.

More specifically, the present invention is defined by [1] to [9] below.

[1] An anti-obesity agent comprising one or more compounds of Formula (1) (except epitheaflagallin, epitheaflagallin-3-O-gallate, theaflavin, theaflavin-3-O-gallate, theaflavin-3'-O-gallate, and theaflavin-3,3'-O-digallate):

[Chemical Formula 1]

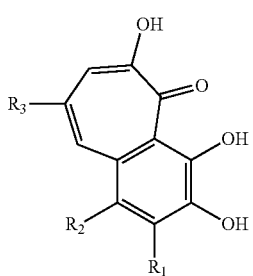

Formula (1)

(wherein R₁ is H or OH;

R₂ is H or a group of Formula (2):

[Chemical Formula 2]

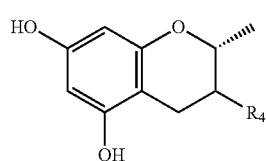

Formula (2)

wherein R₄ is OH or a group of Formula (3):

[Chemical Formula 3]

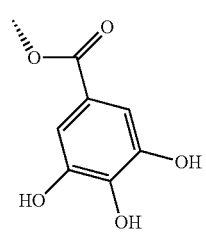

Formula (3)

or a group of Formula (4):

[Chemical Formula 4]

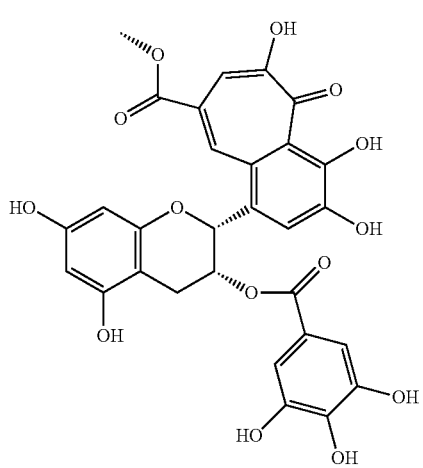

Formula (4)

wherein R₃ is H, COOH, a group of Formula (5):

[Chemical Formula 5]

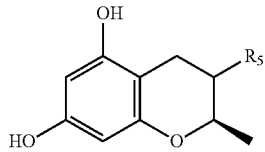

Formula (5)

or a group of Formula (6):

[Chemical Formula 6]

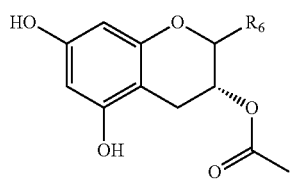

Formula (6)

wherein R₅ is OH, a group of Formula (7):

[Chemical Formula 7]

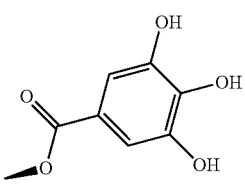

Formula (7)

or a group of Formula (8):

[Chemical Formula 8]

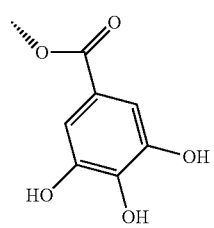

Formula (8)

wherein R₆ is a group of Formula (9):

[Chemical Formula 9]

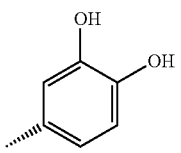

Formula or a group of Formula (10):

[Chemical Formula 10]

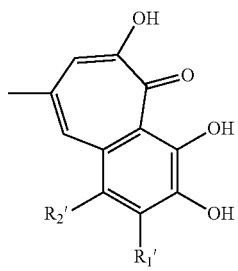

Formula (10)

wherein $R_1'$ is the same group as $R_1$ above and $R_2'$ is a group of Formula (11):

[Chemical Formula 11]

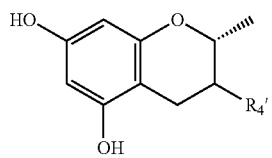

Formula (11)

wherein $R_4'$ is the same group as $R_4$ above).

[2] The anti-obesity agent according to [1], comprising one or more compounds in which $R_1$ is H.

[3] The anti-obesity agent according to [1], wherein the compound is a compound of Formula (12):

[Chemical Formula 12]

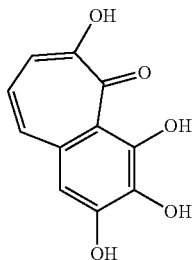

Formula (12)

Formula (13):

[Chemical Formula 13]

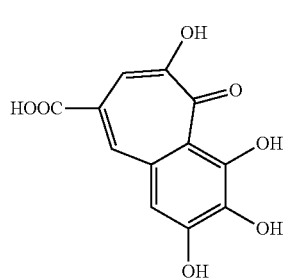

Formula (13)

Formula (14):

[Chemical Formula 14]

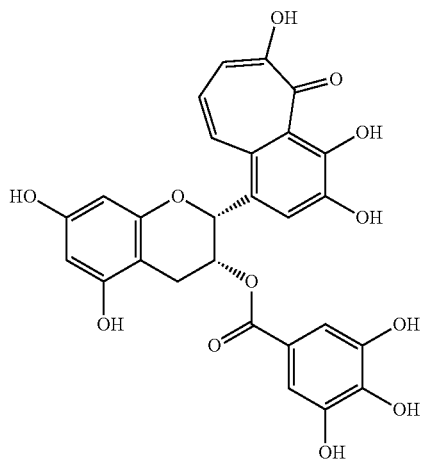

Formula (14)

Formula (15):

[Chemical Formula 15]

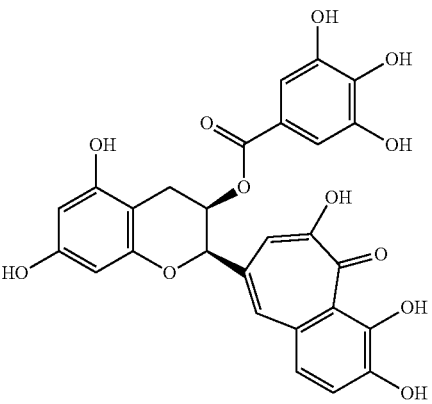

Formula (15)

Formula (16):

[Chemical Formula 16]

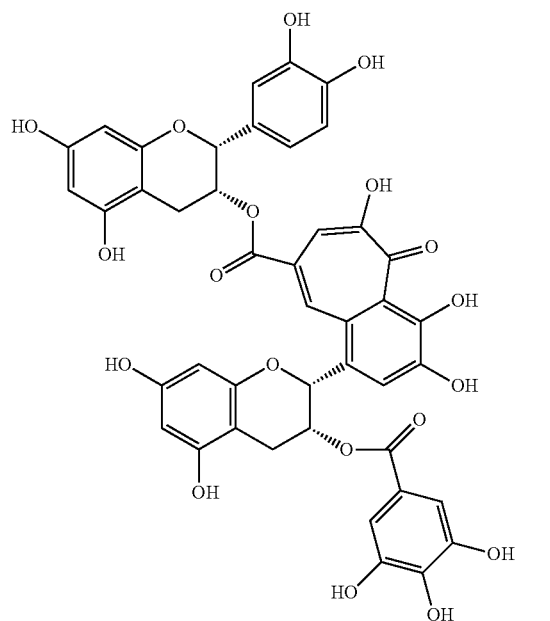

Formula (16)

Formula (17):
[Chemical Formula 17]
Formula (17)
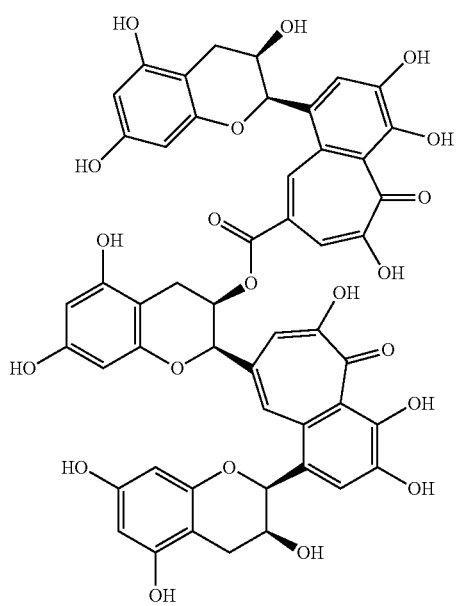
Formula (18):
[Chemical Formula 18]
Formula (18)
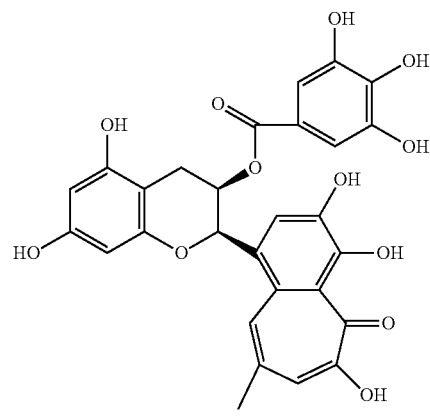
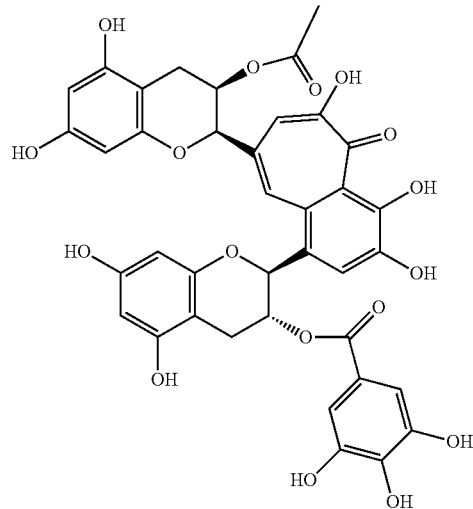
Formula (19):
[Chemical Formula 19]
Formula (19)
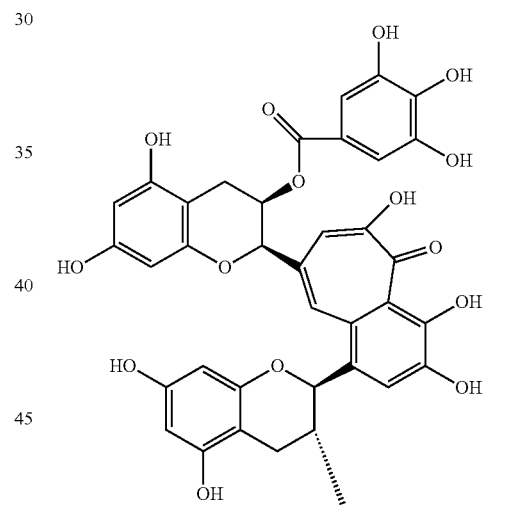

Formula (20):

[Chemical Formula 20]

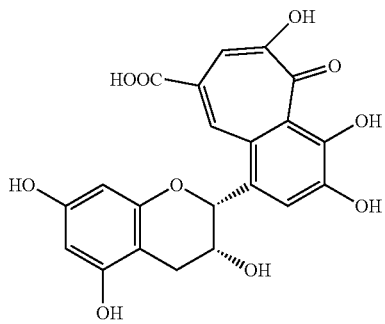

Formula (21):

[Chemical Formula 21]

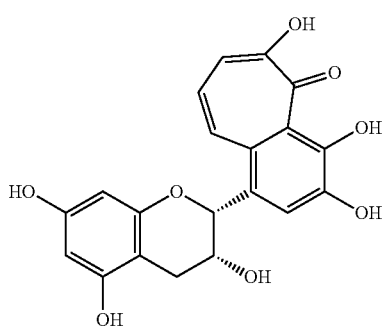

Formula (22):

[Chemical Formula 22]

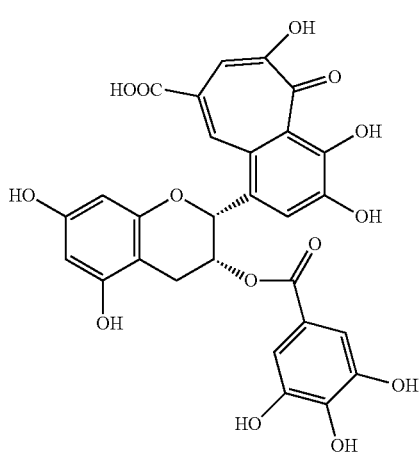

or Formula (23):

[Chemical Formula 23]

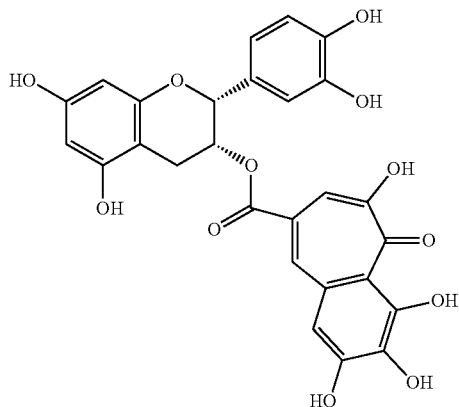

[4] The anti-obesity agent according to any one of [1] to [3], which is a lipase inhibitor and/or an alfa-glucosidase inhibitor.

[5] The anti-obesity agent according to any one of [1] to [4], which is for suppressing absorption of diet-derived fat and sugar.

[6] The anti-obesity agent according to any one of [1] to [5], which is in the form of a food or a beverage.

[7] The anti-obesity agent according to [6], wherein the food or beverage is selected from the group consisting of a tea beverage, a soft drink, and a health food.

[8] The anti-obesity agent according to any one of [1] to [5], which is in the form of a pharmaceutical composition.

[9] A compound of Formula (24):

[Chemical Formula 24]

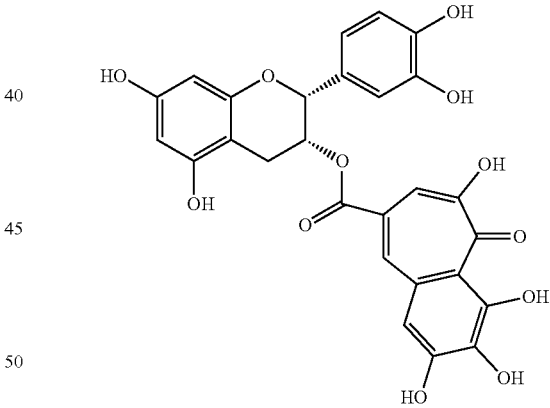

Advantageous Effects of the Invention

The lipase inhibitor that serves as the anti-obesity agent of the present invention contains a tea-derived benzotropolone ring-containing compound and thus exhibits superior lipase inhibitory activity. The lipase inhibitor of the present invention does not compromise the flavor of foods and beverages, has palatability, and can be used in various use applications including foods and beverages intended for reduction in triglycerides and health enhancement. It is desirable to take this inhibitor together with meals for suppression of dietary fat absorption, and therefore, beverages containing tea-derived, enhanced active ingredients are of great significance. Particularly, enhancing these ingredients enabled us to provide a beverage intended for anti-obesity action and health enhancement.

The alfa-glucosidase inhibitor that serves as the anti-obesity agent of the present invention can suppress decomposition of sugar derived from diet-derived starch and polysaccharides and absorption of the sugar, in less amount than conventionally known, natural product-derived alfa-glucosidase inhibitor. Further, all of the compounds are oxides of catechins and polyphenols contained in teas and are thus superior in flavor and safety, which enables long-term intake of the compounds.

In addition, the anti-obesity agent of the present invention contains a benzotropolone ring-containing compound, a component derived from teas, which are widely used in diet, and are thus safe and can be also used as a pharmaceutical composition with reduced side effects.

DESCRIPTION OF EMBODIMENTS

Figure 1:
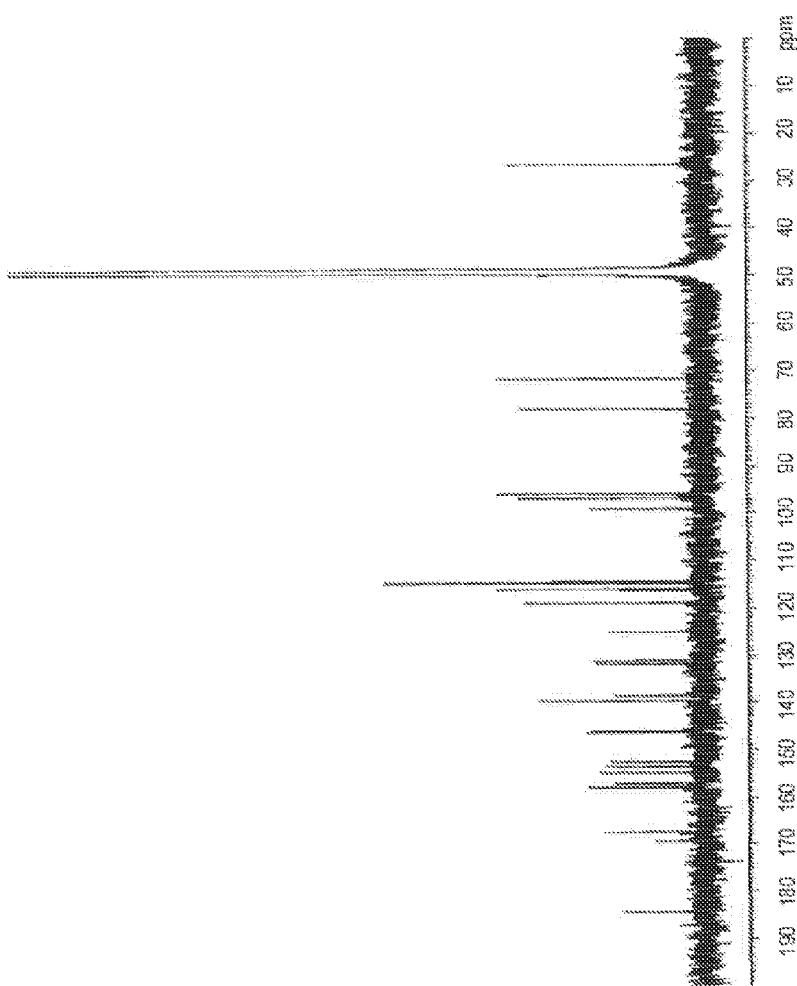
FIG. 1 shows the $^{13}C$ NMR spectrum of Compound 12.

The embodiments of the present invention are described in detail below.

Anti-Obesity Agents

The present invention is an anti-obesity agent containing a benzotropolone ring-containing compound of Formula (1) as an active ingredient:

[Chemical Formula 25]

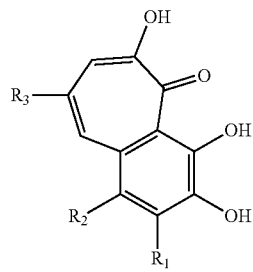

Formula (1)

Particularly, the following is preferred as the active ingredient: purprogallin of Formula (12) below:

[Chemical Formula 26]

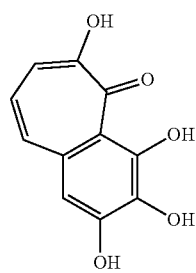

Formula (12)

purprogallin carboxylic acid of Formula (13):

[Chemical Formula 27]

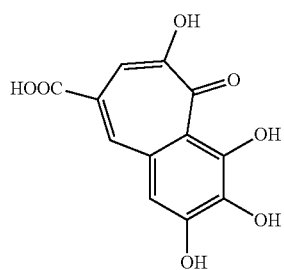

Formula (13)

theaflavanin 3-O-gallate of Formula (14):

[Chemical Formula 28]

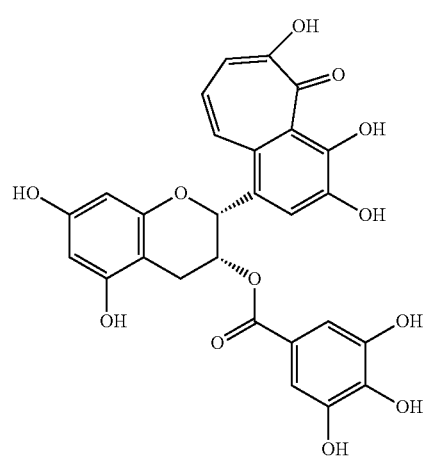

Formula (14)

EGCG-catechol of Formula (15):

[Chemical Formula 29]

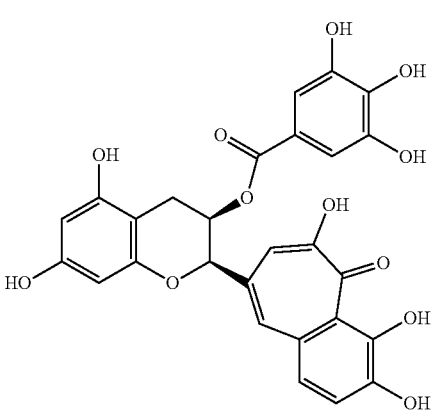

Formula (15)

theaflavate A of Formula (16):
[Chemical Formula 30]
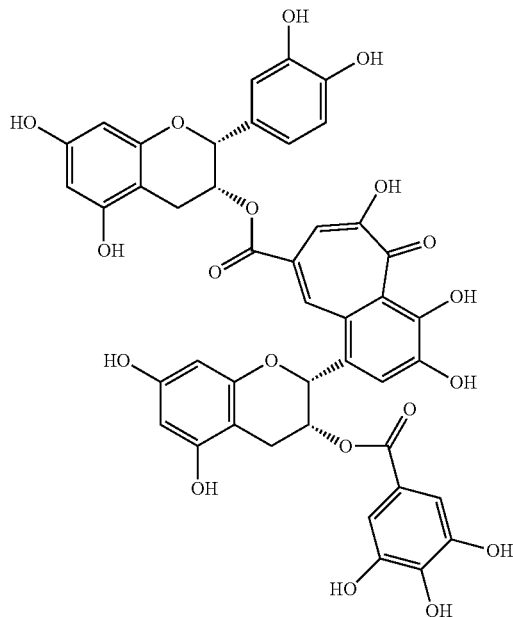
theadibenzotropolone A of Formula (17):
[Chemical Formula 31]
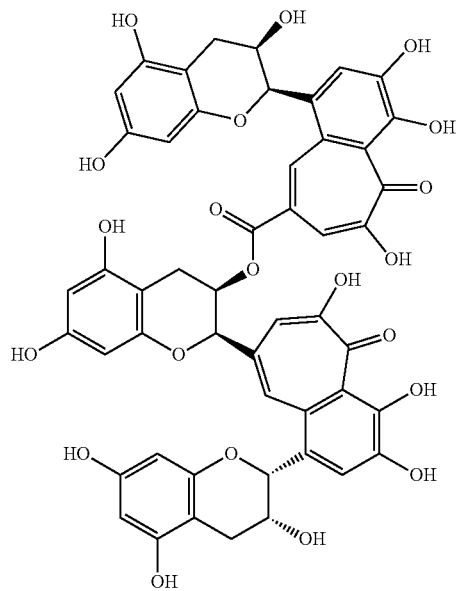
theaflavin digallate trimer 1 (TFdiGA-tri1) of Formula (18):
[Chemical Formula 32]
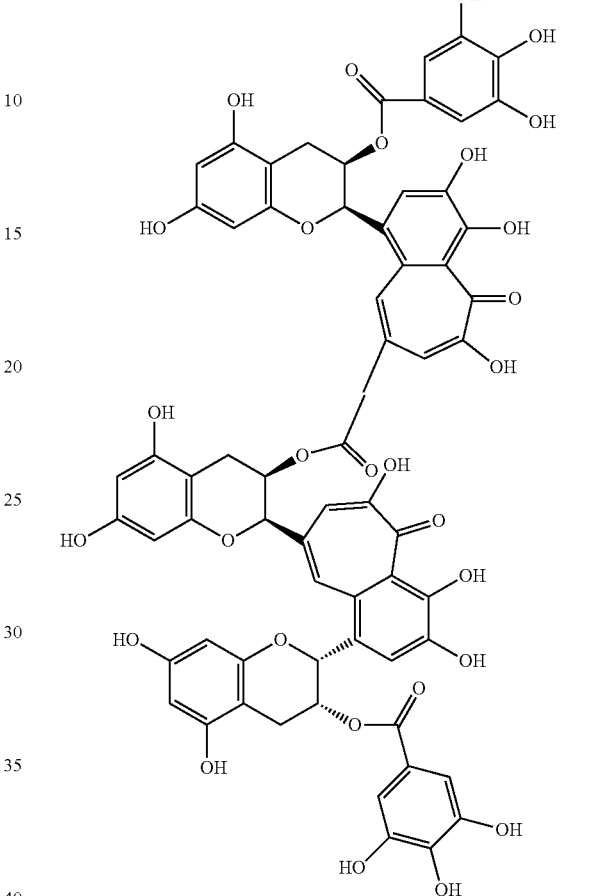
theaflavin digallate trimer 2 (TFdiGA-tri2) of Formula (19):
[Chemical Formula 33]
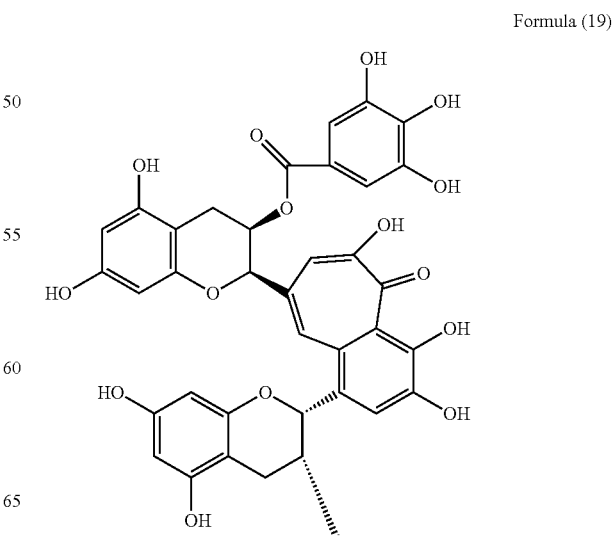

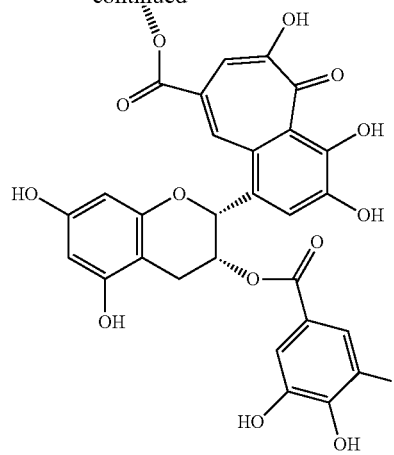

epitheaflavic acid of Formula (20):

[[Chemical Formula 34]]

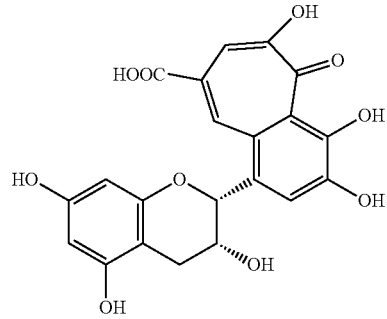

3,4,6-trihydroxy-1-((2R,3R)-3,5,7-trihydroxychroman-2-yl)-5H-benzo[7]annulen-5-one of Formula (21):

[Chemical Formula 35]

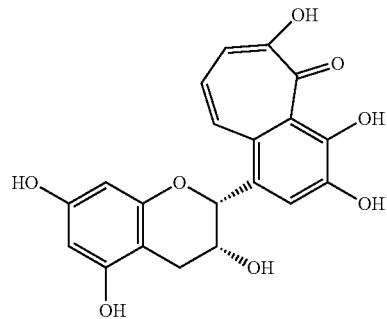

epitheaflavic acid-3-O-gallate of Formula (22):

[Chemical Formula 36]

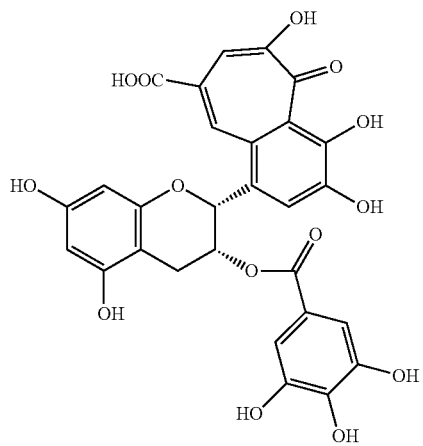

or (2R,3R)-2-(3,4-dihydroxyphenyl)-5,7-dihydroxychroman-3-yl2,3,4,6-tetrahydroxy-5-oxo-5H-benzo[7]annulen-8-carboxylate of Formula (23):

[Chemical Formula 37]

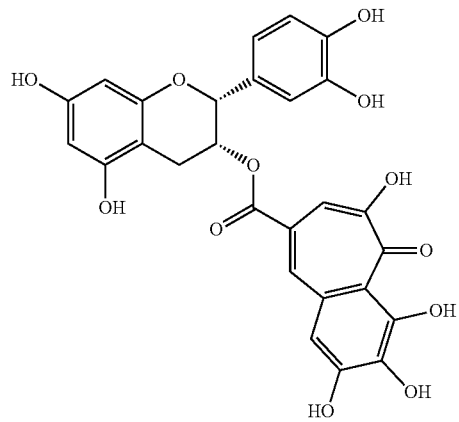

The above benzotropolone ring-containing compounds, which are active ingredients of the anti-obesity agent of the present invention, can be obtained by solvent extraction from natural materials such as green tea, black tea, and oolong tea or also by chemical synthesis or enzymatic synthesis of the materials.

With respect to the natural materials which are extraction raw materials, tea leaves may be used as is or in ground form. The solvent for use in extraction may be water, an organic solvent, mixtures of these solvents, or the like, and preferably, hot water. The extract obtained can be separated and purified by using an adequate carrier for separation. Any carrier can be used if the carrier can absorb the above benzotropolone ring-containing compound and separate it with an adequate solvent for separation. For example, styrene- or dextran-based synthetic adsorbents can be used for the separation and purification. After loading of the above extract on such a carrier, an adequate solvent is used to separate the above benzotropolone ring-containing compound. More specifically, the above benzotropolone ring-containing compound for use in the anti-obesity agent of the present invention can be obtained in accordance with the descriptions in Example 1 of the present specification. The thus obtained benzotropolone ring-containing compound above may be used in condensed form or as a powder obtained by methods such as lyophilization.

The above benzotropolone ring-containing compounds can be synthesized with enzymes such as polyphenol oxidase (PPO) and peroxidase (POD), or with oxidants such as potassium ferricyanide ($K_3[Fe(CN)_6]$) as a catalyst by using, as raw materials, catechins (epigallocatechin-3-O-gallate, epicatechin-3-O-gallate, epicatechin, epigallocatechin, and the like) and gallic acid. Specifically, the synthesis can be performed in accordance with the descriptions in, for example, Examples 2 and 7 of the present specification.

The anti-obesity agent of the present invention has strong inhibitory action against lipase, especially, pancreatic lipase. The lipase inhibitory activity can be measured by any method of the lipase activity assays described in the related applications shown in the Background Art section. For example, the assay can be achieved by using the oleate ester of fluorescent 4-methylumbelliferone as a substrate to measure the fluorescence of 4-methylumbelliferone produced by reaction with lipase. Exemplary is the method described in Example 6, which allows a measurement of lipase inhibitory activity. Lipase inhibitory activity can be expressed, for example, as $IC_{50}$, a sample volume which produces 50% inhibition.

The anti-obesity agent of the present invention have potent alfa-glucosidase inhibitory activity. The activity can be measured by any method of the activity assays described in the related applications shown in the Background Art section. Exemplary is the method described in Example 11, which allows a measurement of alfa-glucosidase inhibitory activity. Alfa-glucosidase inhibitory activity can be expressed, for example, as $IC_{50}$, a sample volume which produces 50% inhibition.

The purified products or partially purified products of the above benzotropolone ring-containing compounds can be used alone as an anti-obesity agent, or can be combined with a solvent or a carrier so as to be used as an anti-obesity agent. It is preferred that the solvent or the carrier can be used safely as a food or a pharmaceutical product, in prospect of use as the foods and beverages below and/or pharmaceutical products. The anti-obesity agent of the present invention has various use applications; exemplary is use of the agent as foods and beverages or pharmaceutical compositions which are used for an experimental study and intended for prevention of triglyceride accumulation.

Foods and Beverages

The anti-obesity agent of the present invention may be in the form of food and beverage that suppresses undesirable elevation of blood triglyceride associated with fat intake from meals. Preferred examples of the food and beverage include those taken on a daily basis; for example, green tea, barley tea, oolong tea, black tea, coffee, sports drinks, drinking water, seasoning, and dressing. However, the foods and beverages also may be those that are commonly consumed: soft drinks, cocktails, beer, whiskey, distilled spirit (shochu), wine, sake, seasoning, dressing, flavored rice, processed foods, instant foods, retort foods, chocolate, fresh cream, Western confectionery, dairy products, health foods, supplements, and the like.

In the anti-obesity agent of the present invention which is in the form of food and beverage, the benzotropolone ring-containing compound of Formula (1) is contained so that the intake of the compound is 0.1 mg to 10 g per meal, preferably, 0.5 mg to 5 g. However, the compound of Formula (1) used in the anti-obesity agent of the present invention is highly safe because it is derived from food, and thus there is no substantial upper limit on the amount of addition to foods and beverages.

Pharmaceutical Composition

The anti-obesity agent of the present invention which serves as a lipase inhibitor can also be used as a pharmaceutical composition intended to suppress diet-derived fat absorption and to prevent undesirable increase of blood triglyceride and/or to lower increased blood triglyceride. The anti-obesity agent which serves as an alfa-glucosidase inhibitor can also be used as a pharmaceutical composition intended to suppress diet-derived fat absorption and to prevent undesirable increase of blood triglyceride and/or to lower increased blood triglyceride. Preferred are agents intended for oral administration; examples of the agent include drinks, tablets, capsules, granules, powders, candies, drops, and the like. The agents contain a benzotropolone ring-containing compound of Formula (1) in amounts of 0.1 mg to 10 g per dose, preferably, 0.5 mg to 5 g.

The pharmaceutical composition of the present invention is safe for long-term dosage due to high safety of lipase and alfa-glucosidase activity of the inhibitory components. Accordingly, the composition can also be taken on a daily basis to prevent or resolve obesity as a lifestyle-related disease.

Novel Compound

Further, the present invention provides a compound shown below as a novel compound present in black tea.

[Chemical Formula 38]

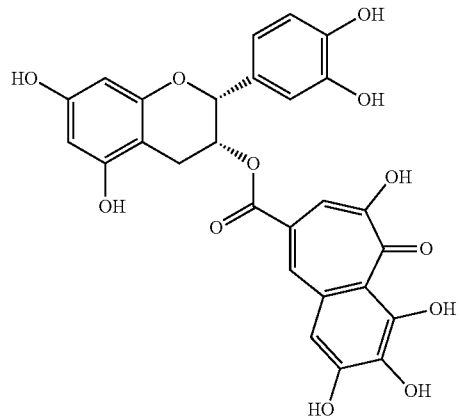

This compound is useful as an anti-obesity material.

The present invention is more specifically described in Examples below, but is not limited thereto.

Example 1

Separation on LH-20

Black tea leaves originated in Assam, India were extracted with hot water at 90° C. and lyophilized, and distilled water was added to the resulting product followed by warming and dissolution to obtain a solution of concentration 10 mg/ml. While heating the solution to 60 to 70° C. in a hot-water bath, 15 ml of the same was loaded on 60 ml of Sephadex LH-20 (GE Healthcare Biosciences, Ltd.) After washing with 45 ml of 20% acetone (acetone:distilled water=2:8, v/v) and subsequent washing with 60 ml (1 column volume) of the same, elution was conducted with 4 column volumes each of the following solvents: 30% acetone (acetone:distilled water=3:7, v/v); 50% acetone (acetone:distilled water=1:1, v/v); and 60% acetone (acetone:distilled water=6:4, v/v), and the resulting solution was fractionated into 1 column volume for each fraction. Two milliliters each taken from a total of fourteen 60 ml fractions was concentrated under vacuum and then 0.1 ml of a 50% aqueous dimethylsulfoxide solution (dimethylsulfoxide:distilled water=1:1, v/v) was prepared, and the solution was subjected to a measurement of lipase inhibitory activity. In addition, each fraction was concentrated under vacuum and lyophilized, and the recovery volume was calculated from the resulting solids; the calculations were used for the component analysis conducted in Example 5. The weights and the recovery rates of lipase inhibitory activity are shown in Table 1.

TABLE 1

Location of Activity in LH20 Fractions

| Fra No. | Fraction | Abundance Ratio of Activity (%) | | Abundance Ratio of Yield (%) | |
|---|---|---|---|---|---|
| 1 | 20% acetone_1 | 0.0005 | 5.0 | 30.6 | 54.3 |
| 2 | 20% acetone_2 | 5.01 | | 23.7 | |
| 3 | 30% acetone_1 | 4.72 | 20.1 | 3.7 | 16.3 |
| 4 | 30% acetone_2 | 6.30 | | 4.7 | |
| 5 | 30% acetone_3 | 5.63 | | 5.1 | |
| 6 | 30% acetone_4 | 3.48 | | 2.8 | |
| 7 | 50% acetone_1 | 14.12 | 70.9 | 4.8 | 23.6 |
| 8 | 50% acetone_2 | 33.59 | | 11.2 | |
| 9 | 50% acetone_3 | 17.08 | | 5.1 | |
| 10 | 50% acetone_4 | 6.15 | | 2.5 | |
| 11 | 60% acetone_1 | 2.53 | 3.9 | 1.3 | 5.8 |
| 12 | 60% acetone_2 | 1.05 | | 1.8 | |
| 13 | 60% acetone_3 | 0.20 | | 1.2 | |
| 14 | 60% acetone_4 | 0.13 | | 1.5 | |

As a result of the measurement of lipase inhibitory activity in accordance with the method described in Example 6, 20% acetone_1 and 20% acetone_2 fractions, which exhibited high yield, were each found to have contained polysaccharides and caffeins and have had almost no activity. On the other hand, in 50% acetone_2 fraction, which exhibited the next highest yield (11.2% by weight), activity of 33.6% was eluted; in the subsequent entry, 50% acetone_3 fraction, activity of 17.1% was eluted. In the 50% acetone elution portions including these fractions, it was found that 70.9% of the activity was eluted. In the assay described in Example 5, many of active benzotropolone ring-containing compounds were eluted with 50% acetone, which is well consistent with the high activity found in 50% acetone elution portions.

Example 2

Syntheses of Test Compounds 1. purprogallin
2. purprogallin carboxylic acid
3. epitheaflagallin
4. epitheaflagallin-3-O-gallate
5. theaflavate A
6. theadibenzotropolone A
7. theaflavin digallate trimer 1 (TFdiGA-tri1)
8. theaflavin digallate trimer 2 (TFdiGA-tri2)
9. epitheaflavic acid
10. theaflavanin
11. epitheaflavic acid-3-O-gallate
12. (2R,3R)-2-(3,4-dihydroxyphenyl)-5,7-dihydroxychroman-3-yl2,3,4,6-tetrahydroxy-5-oxo-5H-benzo[7]annulen-8-carboxylate Syntheses of epitheaflanallin (3) and epitheaflagallin (3) and epitheaflagallin-3-O-gallate (4)

To epigallocatechin (0.2 mmol) (EGC; Wako Pure Chemical Industries, Ltd.) or epigallocatechin-3-O-gallate (0.2 mmol) (EGCG; Wako Pure Chemical Industries, Ltd.), potassium ferricyanide (0.8 mmol) and $NaHCO_3$ (0.8 mmol) were added to prepare 150 ml of an aqueous solution, and the solution was chilled on ice. Fifty milliliters of an aqueous pyrogallol solution (0.2 mmol) was dripped into the solution and stirring the mixture were continued for one hour. The reaction solution was loaded on 20 ml volume of Sep-pak C18 (Waters Corp.), and after washing with 60 ml of water and the subsequent washing with 5% acetonitrile/water, 50% acetonitrile/water containing 0.1% formic acid was used to elute a reaction product. The eluted product was lyophilized and purified by preparative HPLC shown below.

The reaction product of EGC and pyrogallol was loaded on YMC Pak Polymer C-18 (20×300 mm, YMC Co., Ltd.) and an elution with a linear gradient of 30-50% acetonitrile (6 ml/min, 60 minutes) was performed in the presence of 0.1% formic acid. The component eluted at between 48 and 50 minutes was lyophilized to obtain 4 mg of a brown solid (epitheaflagallin (3)). Also, the component eluted at between 68 and 70 minutes in this chromatogram was lyophilized to obtain 2 mg of a brown solid (purpurogallin (1)).

The reaction product of EGCG and pyrogallol was loaded on Develosil C30-UG-5 (20 mm×250 mm, Nomura Chemical Co., Ltd.) and an elution with a linear gradient of 15-50% acetonitrile (6 ml/min, 60 minutes) was performed in the presence of 0.1% formic acid. The component eluted at between 44 and 46 minutes was lyophilized to obtain 6 mg of a brown solid (epitheaflagallin-3-O-gallate (4)). Also, the component eluted at between 48 and 50 minutes in this chromatogram was lyophilized to obtain 3 mg of a brown solid (purpurogallin (1)).

In the same manner as the above reactions, 800 mg of gallic acid was subjected to a reaction to obtain 65 mg of purprogallin carboxylic acid (2), which is produced by polymerization of two gallic acid molecules. In addition, 100 mg of epicatechin-3-O-gallate (ECG) was subjected to a reaction to obtain 3 mg of theaflavate A (5), which is produced by polymerization of two ECG molecules. Further, 400 mg each of epicatechin (EC) and EGCG were subjected to a reaction to obtain a main product, theaflavin-3-O-gallate as well as 2 mg of a by-product, theadibenzotropolone A (6). In the same manner as the above reaction, 200 mg each of epicatechin-3-O-gallate (ECG) and EGCG were subjected to a reaction, and 12 mg of the resulting theaflavin-3,3'-digallate and 20 mg of ECG were subjected to a reaction to obtain 1.7 mg of TFdiGA-tri1 (7) and 0.6 mg of TFdiGA-tri2 (8). The following compounds were also obtained: 48 mg of epitheaflavic acid (9) obtained by reaction of 330 mg of gallic acid and 101 mg of EC; 12 mg of theaflavanin (10) obtained by reaction of 869 mg of pyrogallol and 400 mg of EC; and 37 mg of epitheaflavic acid-3-O-gallate (11) and 3.3 mg of (2R,3R)-2-(3,4-dihydroxyphenyl)-5,7-dihydroxychroman-3-yl2,3,4,6-tetrahydroxy-5-oxo-5H-benzo[7]annulen-8-carboxylate (12) which were simultaneously obtained by reaction of 470 mg of gallic acid and 221 mg of ECG.

Example 3

Structural Analyses of Compounds

MS and NMR measurements of the compounds obtained in Example 2 were performed. Their mass spectra were determined with Q-TOF Premier (Micromass Co., Ltd., UK) using Z-Spray ESI ion source, in negative, V mode. Cone voltage: 45V, Capillary voltage: 3 KV, Source Temp.: 80° C., Desolvation Temp.: 180° C. Mass correction was performed with LockSpray, and leucine enkepharine (m/z 554.2615 [M-H]) was used as a reference.

The accurate mass, molecular formula, and theoretical mass value of each compound are shown in Table 2.

TABLE 2

Mass Spectrometric Results of Compounds

| Compound No. | Compound | m/z Actual Mass Value | Molecular Formula | ma/z Calc. Value |
|---|---|---|---|---|
| 1 | Purprogallin | 219.0285 | C11H8O5 | 219.0293 |
| 2 | purprogallin carboxylic acid | 263.0183 | C12H8O7 | 263.0192 |
| 3 | epitheaflagallin | 399.0701 | C20H16O9 | 399.0716 |
| 4 | epitheaflagallin-3-O-gallate | 551.0818 | C27H20O13 | 551.0826 |
| 5 | theaflavateA | 851.1471 | C43H32O19 | 851.1460 |
| 6 | theadibenzotropoloneA | 973.1832 | C50H38O21 | 973.1827 |
| 7 | TFdiGA-tri1 | 1279.2185 | C64H46O29 | 1279.2203 |
| 8 | TFdiGA-tri2 | 1279.2218 | C64H46O29 | 1279.2203 |
| 9 | epitheaflavic acid | 427.0686 | C21H16O10 | 427.0665 |
| 10 | theaflavanin | 383.0784 | C20H16O8 | 383.0767 |
| 11 | epitheaflavic acid-3-O-gallate | 579.0778 | C28H20O14 | 579.0775 |
| 12 | (2R,3R)-2-(3,4-dihydroxyphenyl)-5,7-dihydroxychroman-3-yl 2,3,4,6-tetrahydroxy-5-oxo-5H-benzo[7]annulene-8-carboxylate | 535.0883 | C27H20O12 | 535.0877 |
| 14 | theaflavanin-3-O-gallate | 535.0871 | C27H20O12 | 535.0877 |
| 15 | EGCG-catechol | 535.0885 | C27H20O12 | 535.0877 |

Example 4

Quantification in Tea Leaf Extract

The LC-MS/MS measurements were performed with 4000 Q TRAP (Applied Biosystems Inc.) using TurboIonSpray in negative mode under the following conditions: Collision energy: 46 eV (nega.); Ionspray voltage: 4500V; Temperature: 450° C.

The elution time and measurement channels of each compound in MRM (multiple reaction monitoring) mode are as shown in Table 3.

TABLE 3

LC-MSMS Quantitative Parameters

| Compound | Compound | R.T. | Q1/Q3 |
|---|---|---|---|
| 1 | purprogallin | 10.99 | 219.0/191.0 |
| 2 | purprogallin carboxylic acid | 8.01 | 263.0/190.9 |
| 3 | epitheaflagallin | 8.64 | 399.1/233.0 |
| 4 | epitheaflagallin-3-O-gallate | 11.54 | 551.1/233.1 |
| 5 | theaflavateA | 14.46 | 851.2/579.1 |
| 6 | theadibenzotropoloneA | 11.49 | 973.2/227.1 |
| 7 | TFdiGA-tri1 | 15.01 | 1277.2/579.1 |
| 8 | TFdiGA-tri2 | 17.37 | 1277.2/697.1 |

Column: YMC-Polymer C18, S-6 μm (YMC Co., Ltd., 2 mmφ×150 mm)

Flow Rate: 0.2 mL/min

Column Temp.: 40° C.

Mobile Phase A: 0.1V/V % HCOOH/H$_2$O

Mobile Phase B: 0.1 V/V % HCOOH/CH$_3$CN

Gradient Program: A/B=91/9 (0 min)→A/B=40/60 (17 min)→A/B=15/85 (17.1 min)→A/B=15/85 (17.1 to 19 min)

The above conditions were used to assay a hot water extract of Indian Assam CTC tea. Compounds 2 to 8 were found to have been present in the tea leaves. The quantitative values are shown in Table 4.

TABLE 4

Quantitative Values of Black Tea Components

| Compound | Compoun | μg/g extract |
|---|---|---|
| 1 | purprogallin | 0.15 |
| 2 | purprogallin carboxylic acid | 166.00 |
| 3 | epitheaflagallin | 224.00 |
| 4 | epitheaflagallin-3-O-gallate | 369.0 |
| 5 | theaflavateA | 165.5 |
| 6 | theadibenzotropoloneA | 35.95 |
| 7 | TFdiGA-tri1 | 67.20 |
| 8 | TFdiGA-tri2 | 61.55 |

Example 5

Distribution of Each Compound in Tea Leaf Fraction

LC-MS/MS measurements were performed with Q-TOF Premier (Micromass Co., Ltd., UK) using Z-Spray ESI ion source, in negative, V mode. Cone voltage: 33V, Capillary voltage: 3 KV, Source Temp.: 150° C., Desolvation Temp.: 250° C. Mass correction was performed with LockSpray, and leucine enkepharine (m/z 554.2615 [M-H]$^-$) was used as a reference.

Column: YMC-Polymer C18, S-6 μm (YMC Co., Ltd., 2 mmφ×150 mm)

Flow Rate: 0.2 mL/min

Column Temp.: 40° C.

Mobile Phase A: 0.1V/V % HCOOH/H$_2$O

Mobile Phase B: 0.1V/V % HCOOH/CH$_3$CN

Gradient Program: A/B=70/30→A/B=50/50 (20 min)→A/B=50/50 (25 min)

The above conditions were used to analyze each of the fractions of tea leaves originated in Assam, India, which were obtained by fractionation in Example 1. Compound 2 (m/z 263.02, R.T.=9.29 min) was detected in 30% acetone_1 fraction, Compound 3 (m/z 399.07, R.T.=9.83 min) was in 50% acetone_2 and 50% acetone_3 fractions, Compound 4 (m/z 551.08, R.T.=13.48 min) was in 50% acetone_3 and 50% acetone_4 fractions, Compound 5 (m/z 851.15, R.T.=17.50 min) was in 50% acetone_4 fraction, Compound 9 (m/z 427.07, R.T.=8.60 min) was in 50% acetone_3 fraction, Compound 10 (m/z 383.08, R.T.=9.65 min) was in 30% acetone_3 and 30% acetone_4 fractions, Compound 11 (m/z 579.08, R.T.=13.86 min) was in 50% acetone_2 fraction, and Compound 12 (m/z 535.09, R.T.=13.90 min) was in 50% acetone_2 fraction.

Example 6

Measurement of Lipase Inhibitory Activity

Measurement samples were synthesized and purified in accordance with the method in Example 2.
1. purprogallin
2. purprogallin carboxylic acid
5. theaflavate A
6. theadibenzotropolone A
7. theaflavin digallate trimer 1 (TFdiGA-tri1)
8. theaflavin digallate trimer 2 (TFdiGA-tri2)
9. epitheaflavic acid
10. theaflavanin
11. epitheaflavic acid-3-O-gallate
12. (2R,3R)-2-(3,4-dihydroxyphenyl)-5,7-dihydroxychroman-3-yl2,3,4,6-tetrahydroxy-5-oxo-5H-benzo[7]annulen-8-carboxylate
13. EGCG (Wako Pure Chemical Industries, Ltd.)

Method of Measurement

The measurement of lipase activity was performed by using as a substrate the oleate ester of fluorescent 4-methylumbelliferone (4-MUO; Sigma-Aldrich Corp.) to measure the fluorescence of 4-methylumbelliferone produced by a reaction. In the measurement, 13 mM Tris-HCl (pH8.0) containing 150 mM NaCl and 1.36 mM $CaCl_2$ was used as a buffer. The following were subjected to an enzymatic measurement: the substrate 4-MUO which was dissolved into a 0.1M DMSO solution followed by dilution of the solution 4000-fold with the above buffer; and as a lipase, porcine pancreatic lipase (Sigma-Aldrich Corp.) which was prepared as a 400 U/ml solution by using the above buffer likewise.

An enzymatic reaction was initiated by the following steps under 25° C. condition: adding to a 96-well microplate 50 μl of a 4-MUO buffer solution and 25 μl of distilled water (or an aqueous sample solution) for each well; mixing them; and then adding 25 μl of a lipase buffer solution to each well. After a 30-minute reaction, 100 μl of a 0.1M citric acid buffer (pH4.2) was added to terminate the reaction, and the fluorescence of 4-methylumbelliferone (excitation wavelength: 355 nm, fluorescence wavelength: 460 nm) produced by the reaction was measured with a fluorescence plate reader (Fluoroskan Asent CF from Labsystems, Inc.)

The inhibitory activity of test samples were determined as $IC_{50}$ (μM), a sample volume which produces 50% inhibition, relative to the activity of a control (distilled water).

Results

The lipase inhibitory activity of Compounds 1, 2, and 5 to 14 is shown in Table 5.

TABLE 5

Lipase Inhibitory Activity per mole

| Compound No. | Compound | IC50 μM |
|---|---|---|
| — | pyrogallol | 17.273 |
| 1 | purprogallin | 0.413 |
| 2 | purprogallin carboxylic acid | 4.165 |
| 5 | theaflavateA | 0.202 |
| 6 | theadibenzotropoloneA | 0.178 |
| 7 | TFdiGA-tri1 | 0.135 |
| 8 | TFdiGA-tri2 | 0.138 |
| 9 | epitheaflavic acid | 4.626 |
| 10 | theaflavanin | 0.984 |
| 11 | epitheaflavic acid 3-O-gallate | 0.266 |
| 12 | (2R,3R)-2-(3,4-dihydroxyphenyl)-5,7-dihydroxychroman-3-yl 2,3,4,6-tetrahydroxy-5-oxo-5H-benzo[7]annulene-6-carboxylate | 0.207 |
| 13 | EGCG | 0.349 |

All of the benzotropolone ring-containing compounds exhibited lipase inhibitory activity. In (−)-epigallocatechin-3-O-gallate (EGCG; Compound 13), which is known to exhibit strong lipase inhibition, its $IC_{50}$ was 0.349 μM. The compounds other than purprogallin carboxylic acid (2) and epitheaflavic acid (9) which have a free carboxylic acid residue exhibited activity equivalent to or stronger than EGCG, which showed that their benzotropolone ring contributes to their lipase inhibitory activity. A carboxylic acid residue was found to serve to reduce the activity. Accordingly, in Formula (1), $R_3$ is preferably a group other than COOH.

Example 7

(1) Preparations of Compounds

Syntheses of Compounds 12 and 14 (theaflavanin 3-O-gallate) with Peroxidase

Used were horseradish peroxidase from Zymed Laboratories, Inc. as a peroxidase, epicatechin 3-O-gallate (ECG) of 90% purity or higher, which was purified by reversed-phase HPLC from tea extract, and pyrogallol from Nacalai Tesque, Inc. (99.0% purity).

(2) Reactions

In 10 ml of a 0.058 M acetic acid buffer, 4.3 mg of the horseradish peroxidase was dissolved, and to this solution, 250 mg of ECG (0.566 mmol) dissolved in 500 μl of acetone and 192.8 mg of pyrogallol (1.53 mmol) dissolved in 500 μl of acetone were added followed by stirring. Under 30° C. condition, 450 μl of a 3% (w/v) hydrogen peroxide solution was added to initiate a reaction. For improvement of reaction efficiency, 450 μl of a 3% (w/v) hydrogen peroxide solution was added twice, i.e., after 10 and 20 minutes of the reaction initiation. Added were 192.8 mg of pyrogallol (1.53 mmol) and 450 μl of a 3% hydrogen peroxide solution after 30 minutes of the reaction initiation, and then reacted for another 30 minutes.

After 60 minutes of the reaction initiation, the reaction solution was loaded on a reversed-phase stationary phase (Waters Corp., Sep-Pak, C18-Vac 20 cc (5 g)) followed by washing with 40 ml of distilled water. Consecutive elutions were then performed with 20 ml of a 20% (v/v) aqueous acetonitrile solution and then with 40 ml of a 70% (v/v) aqueous acetonitrile solution. The 70% acetonitrile eluate was concentrated and lyophilized to obtain 68.0 mg of a fraction containing Compounds 12 and 14 (theaflavanin 3-O-gallate).

The mixture containing Compounds 12 and 14 (theaflavanin 3-O-gallate) was purified by HPLC under the conditions below.

The mixture was loaded on YMC-Pak Polymer C-18 (20×300 mm, YMC Co., Ltd.), and in the presence of 0.1% formic acid, a 30-minute isocratic elution with 30% acetonitrile and then an elution with a linear gradient of 30-45% acetonitrile (6 ml/min, 150 minutes) were performed. The component eluted at between 144 and 148 minutes and that eluted at between 158 and 162 minutes were lyophilized to obtain 3.9 mg of the compound identical to Compound 12 shown in Example 2 and 3.0 mg of Compound 14 (theaflavanin 3-O-gallate). Further, the component eluted at between 108 and 113 minutes in this chromatogram was lyophilized to obtain 36 mg of a brown solid (Compound 1 in Example 2: purprogallin).

Example 8

Instrumental and Structural Analyses of Reaction Products

Compounds 12 and 14, which were obtained in Example 7, were subjected to MS and NMR measurements.

Their mass spectra were determined with Q-TOF Premier (Micromass Co., Ltd., UK) using Z-Spray ESI ion source, in negative, V mode. Cone volt.: 33 V, Capillary voltage: 2.7 kV, Source Temp.: 80° C., Desolvation Temp.: 180° C. Mass correction was performed with LockSpray, and leucine enkepharine (m/z 554.2615 [M-H]$^-$) was used as a reference. The collision energy was set at 4 eV at the time of MS measurement and at 22 eV at the time of MS/MS measurement.

Compounds 12 and 14 produced molecular ions of m/z 535.0883 and 535.0871 [M-H]−, respectively, and their molecular formula was determined as $C_{27}H_{20}O_{12}$ (theoretical value: 535.0877). As a result of the MS/MS measurement in which collision energy was set at 22 eV, fragment ions of 263.07 and 219.07 were detected in Compound 12 and those of 383.08 and 169.01 were in Compound 14. Compound 14 was found to be a known compound, theaflavanin 3-O-gallate.

Figure 2:
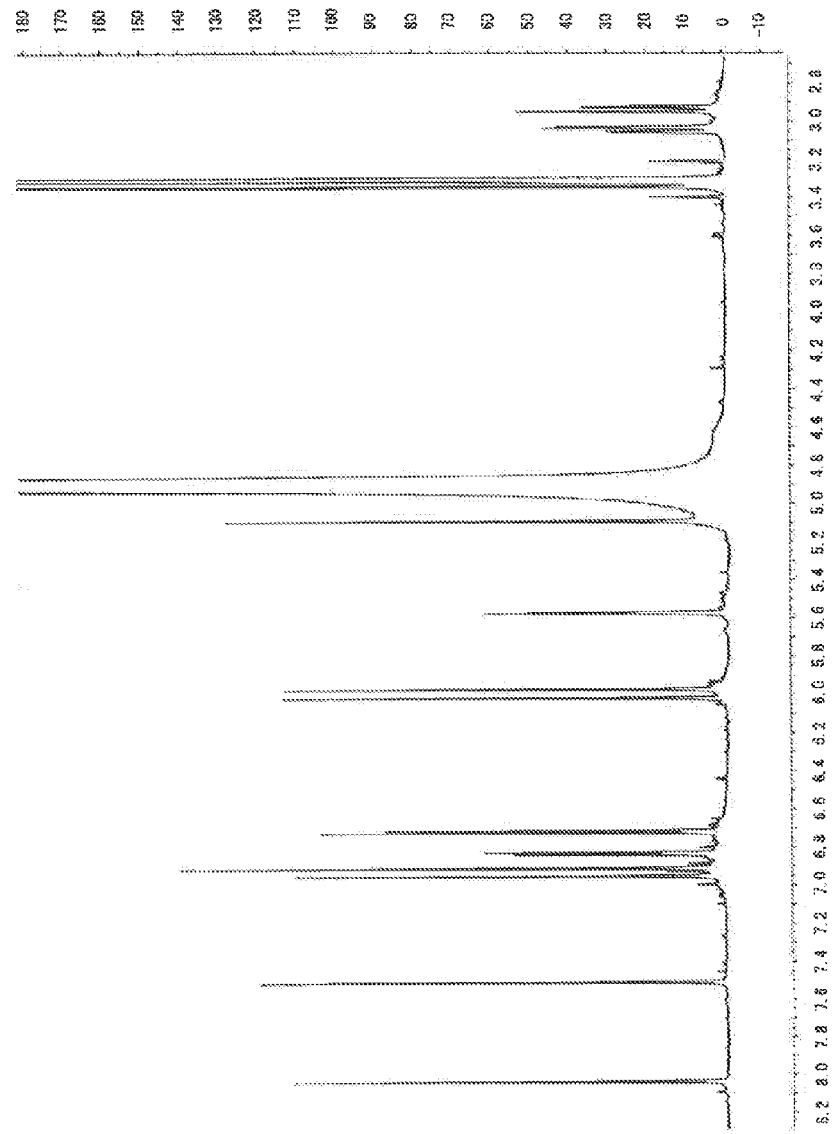
FIG. 2 shows the $^{1}H$ NMR spectrum of Compound 12.

An NMR measurement was performed to confirm the structure of Compound 12. The $^{13}C$ NMR and $^1H$ NMR spectra of Compound 12 are shown in FIGS. 1 and 2, respectively. The NMR measurement was performed under the conditions below. In $CD_3OH$, 3 mg of Compound 12 obtained in Example 7 was dissolved, and the residual peaks of protons and $^{13}C$ of $CD_3OH$, 83.30 and 848.97, were set as internal standards. Measurements in accordance with the following methods were performed with a DMX-750 spectrometer (BRUKER BIOSPIN, Germany): $^1H$ NMR, $^{13}C$ NMR, $^1H\{^{13}C\}$-HSQC, $^1H\{^{13}C\}$-HMBC, TOCSY, DQF-COSY, NOESY, and ROESY. As a result, Compound 12, which was obtained in Example 7, was confirmed to have the structure shown below.

[Chemical Formula 39]

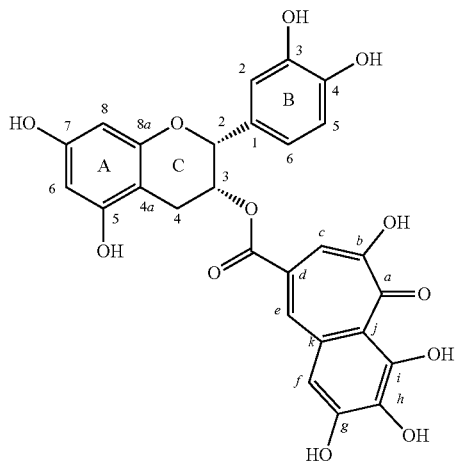

The numbering of each atom is shown in the above structural formula.

The NMR measurement results and the signal assignments are shown below.

TABLE 6

| | | $^1H$ | | $^{13}C$ |
|---|---|---|---|---|
| | | δ | J (Hz) | δ |
| A(C)-ring | C-2 | 5.09 brs | | 78.23 |
| | C-3 | 5.58 dd | | 71.75 |
| | C-4 | 2.94 dd | 17.4, 1.9 | 26.48 |
| | A-5 | 3.04 dd | 17.4, 4.5 | 157.07 |
| | A-6 | 6.02 d | 22 | 96.75 |
| | A-7 | OH | | 157.91 |
| | A-8 | 5.97 d | | 95.8 |
| | A-8a | | | 158.07 |
| | C-4a | | | 99.07 |
| B-ring | B-1 | | | 131.25 |
| | B-2 | 6.95 d | 1.4 | 114.76 |
| | B-3 | OH | | 146.25 |
| | B-4 | OH | | 146.11 |
| | B-5 | 8.72 d | 8 | 116.04 |
| | B-6 | 6.83 dd | 8, 1.4 | 118.87 |
| benzotropolon | a | C=O | | 184.35 |
| | b | OH | | 154.63 |
| | c | 7.51 d | 1 | 114.45 |
| | d | | | 125.12 |
| | e | 8.03 brs | | 139.62 |
| | f | 6.91 s | | 114.76 |
| | g | OH | | 152.62 |
| | h | OH | | 138.44 |
| | i | OH | | 153.73 |
| | j | | | 116.29 |
| | k | | | 131.96 |

The structure of Compound 14 is also shown below.

[Chemical Formula 40]

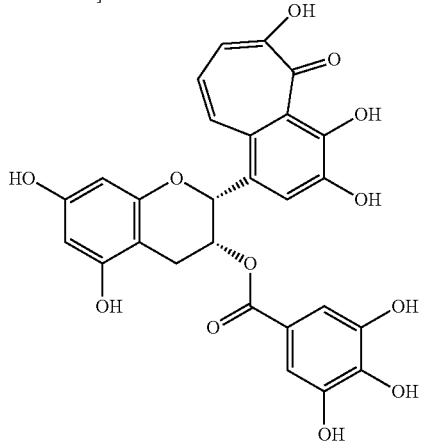

Synthesis of Compound 15

To 229.2 mg of epigallocatechin-3-O-gallate (0.5 mmol) (EGCG; Wako Pure Chemical Industries, Ltd.), 3.293 g of potassium ferricyanide (10 mmol) (Nacalai Tesque, Inc.) and 0.84 g of NaHCO$_3$ (10 mmol) were added to prepare 400 ml of an aqueous solution, and the solution was chilled on ice. Into the solution, 100 ml of an aqueous solution of 275.3 mg of catechol (2.5 mmol) was dripped over one hour, and the mixture was kept stirred. The reaction solution was loaded on 300 mL of Sephadex LH-20 (GE Healthcare Biosciences, Ltd.) and elutions were performed with 1 L of 40% acetone/water, 1.2 L of 45% acetone/water, and 900 mL of 50% acetone/water, consecutively, followed by lyophilization. Consequently, 77 mg of a 45% fraction containing EGCG-catechol was obtained. The fraction was purified by preparative HPLC shown below.

The fraction containing EGCG-catechol was loaded on YMC-Pak Polymer C-18 (20×300 mm, YMC Co., Ltd.), and at a flow rate of 6 ml/min in the presence of 0.1% formic acid, an elution with a linear gradient of 25-45% acetonitrile (75 minutes) was performed, and then a 30-minute isocratic elution was maintained with 45% acetonitrile. The component eluted at between 92 and 95 minutes was lyophilized to obtain 24 mg of a brown solid (Compound 15: EGCG-catechol). The structure of Compound 15 is shown below.

[Chemical Formula 41]

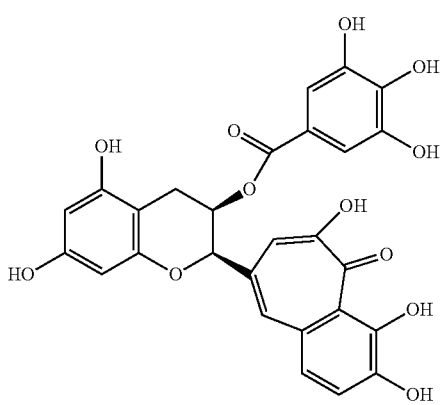

Example 10

Measurement of Lipase Activity

Method of Measurement

The measurement of lipase activity was performed by using as a substrate the oleate ester of fluorescent 4-methylumbelliferone (4-MUO; Sigma-Aldrich Corp.) to measure the fluorescence of 4-methylumbelliferone produced by a reaction. In the measurement, 13 mM Tris-HCl (pH8.0) containing 150 mM NaCl and 1.36 mM CaCl$_2$ was used as a buffer. The following were subjected to an enzymatic measurement: the substrate 4-MUO which was dissolved into a 0.01M DMSO solution followed by dilution of the solution 667-fold with the above buffer; and as a lipase, porcine pancreatic lipase (Sigma-Aldrich Corp.: Type VI-S) which was prepared as a 400 U/ml solution by using the above buffer likewise.

An enzymatic reaction was initiated by the following steps under 25° C. condition: adding to a 96-well microplate 50 µl of 4-MUO buffer solution and 25 µl of distilled water (or aqueous sample solution) for each well; mixing them; and then adding 25 µl of a lipase buffer solution to each well. This measurement was designed to increase the solubility of the substrate to enable inhibitory activity to be measured more accurately, because the concentration of the substrate was 7.5 µM at the time of the reaction, which showed its dilution as compared with the concentration 12.5 µM achieved in Example 6 and the DMSO concentration was increased. After a 30-minute reaction, 100 µl of 0.1M citric acid buffer (pH4.2) was added to terminate the reaction, and the fluorescence of 4-methylumbelliferone (excitation wavelength: 355 nm, fluorescence wavelength: 460 nm) produced by the reaction was measured with a fluorescence plate reader (Fluoroskan Asent CF from Labsystems, Inc.).

The inhibitory activities of test samples were determined as IC$_{50}$ (µM), a sample volume which produces 50% inhibition, relative to the activity of a control (distilled water).

The lipase inhibitory activity of Compounds 3, 4, 12, 13, 14, and 15 was measured. The results are shown in Table 7.

TABLE 7

| Lipase Inhibitory Activity per Mole | | |
|---|---|---|
| Compound | Compound | IC50 µM |
| 3 | epitheaflagalin | 0.956 |
| 4 | epitheaflagalin 3-O-gallate | 0.125 |
| 12 | (2R,3R)-2-(3,4-dihydroxyphenyl)-5,7-dihydroxychroman-3-yl 2,3,4,6-tetrahydroxy-5-oxo-5H-benzo[7]annulene-8-carboxylate | 0.096 |
| 13 | EGCG | 0.349 |
| 14 | theaflavanin 3-O-gallate | 0.168 |
| 15 | EGCG-catechol | 0.104 |

Compounds 12, 14, and 15 all had stronger activity than a positive control, EGCG, and exhibited activity equivalent to or stronger than Compound 4 (Japanese Patent Public Disclosure 2009-114079), which is known as a lipase inhibitor.

The structures of Compounds 14 and 15 are shown as antioxidants and anti-inflammatory pharmaceutical agents in Japanese Patent Public Disclosure 2007-504168, but their lipase and alfa-glucosidase inhibitions were not known.

Compounds 12 and 14 can be synthesized by using polyphenol oxidase (PPO) or oxidants such as potassium ferricyanide besides the enzyme shown in Examples. Also, the compounds can be synthesized not only by a combination of ECG and pyrogallol but also by reaction with gallic acid.

Example 11

Measurement of Alfa-Glucosidase Inhibitory Activity of Various Benzotropolone Ring-Containing Compounds A 1M sodium phosphate buffer was prepared by mixing a 0.1M $NaH_2PO_4\text{-}2H_2O$ and a 0.1M $Na_2HPO_4.12H_2O$ and adjusting the mixture to pH7.0, and thereto 2 g/L of bovine serum albumin (Nacalai Tesque, Inc., F-V, pH5.2, 96% purity) and 0.2 g/L of $NaN_3$ (Nacalai Tesque, Inc., a special grade reagent) were added. To prepare an enzyme solution, alfa-glucosidase (Wako Pure Chemical Industries, Ltd., yeast-derived, 100 units/mg) was dissolved in the above buffer so as to achieve 0.5 units/mg protein/ml (100 μg/20 ml). To prepare a substrate solution, p-nitrophenyl-alfa-D-glucopyranoside (Nacalai Tesque, Inc., a special grade reagent) was dissolved in the above buffer so as to achieve 5 mM concentration (7.525 mg/5 ml).

Among the samples used for the assays, epigallocatechin-3-O-gallate (Compound 13: EGCG), a positive control, was a product from Wako Pure Chemical Industries, Ltd., and Compounds 1, 3, 4, 5, 11, 12, 14, and 15 were products that were synthesized and purified in Example 1, 2, or 7.

These samples were adjusted so as to obtain 10 mg/ml of DMSO and the solution was diluted 2-fold in 6 steps. Using a 96-well microplate, 45 μL of the enzyme solution was added to 10 μL of the sample solution. After preincubation at 37° C. for 5 minutes, 45 μL of the substrate solution was added and absorbance at 405 nm (A405 nm) was measured. After incubation at 37° C. for 5 minutes, the absorbance A405 nm was measured. Percent inhibition was calculated as a difference in A405 nm from a solution in which only DMSO was added as a control instead of a sample, and two consecutive measurements were performed for activity of each compound.

As a result, the alfa-glucosidase inhibitory activity of each Compound, when indicated by $IC_{50}$ value, is as shown in Table 8; Compounds 12 and 14 exhibited particularly strong activity.

TABLE 8 alfa-glucosidase inhibitory activity

| Compound | Compound | IC50 (mM) |
|---|---|---|
| 1 | purpurogallin | 1.237 |
| 3 | epitheaflagallin | No |
| 4 | epitheaflagallin 3-O-gallate | 0.180 |
| 5 | theaflavate A | 0.116 |
| 11 | epitheaflavic acid-GA | 0.287 |
| 12 | (2R,3R)-2-(3,4-dihydroxyphenyl)-5,7-dihydroxychroman-3-yl 2,3,4,6-tetrahydroxy-5-oxo-5H-benzo[7]annulene-8-carboxylate | 0.159 |
| 13 | EGCG | 0.485 |
| 14 | theaflavanin 3-O-gallate | 0.196 |
| 15 | EGCG-catechol | 0.103 |

From these results, together with the results on lipase inhibitory activity, these benzotropolone ring-containing compounds were found to have strong inhibitory activities against digestive enzymes. Among all, Compound 12, which exhibited its strong inhibitory activities against both the two enzymes, was confirmed to be present also in black tea; to date, the compound has not been known, but was found to be useful as an anti-obesity material.

INDUSTRIAL APPLICABILITY

The anti-obesity agent of the present invention contains a tea-derived benzotropolone ring-containing compound and thus exhibits superior inhibitory activities against lipase and alfa-glucosidase. The agent does not compromise the flavor of foods and beverages, has palatability, and can be used in various use applications including foods and beverages intended for health enhancement such as reduction in triglycerides.

The invention claimed is:
1. A method of inhibiting lipase activity comprising: administering one or more compounds of Formula (1) to a subject in need thereof, wherein the compounds of Formula (1) are selected from:

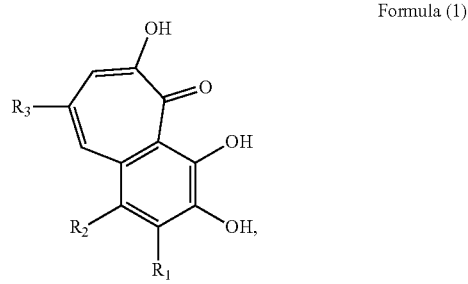

Formula (1)

wherein $R_1$ is H or OH;
$R_2$ is H or a group of Formula (2):

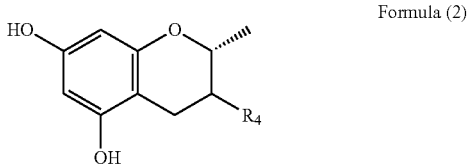

Formula (2)

wherein $R_4$ is OH, a group of Formula (3):

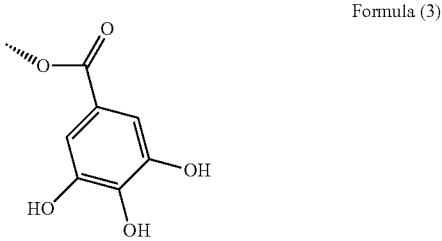

Formula (3)

or a group of Formula (4):

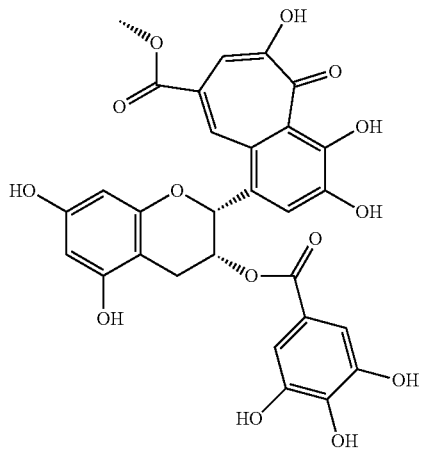
Formula (4)

$R_3$ is COOH, a group of Formula (5):

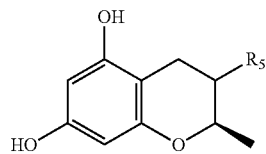
Formula (5)

or a group of Formula (6):

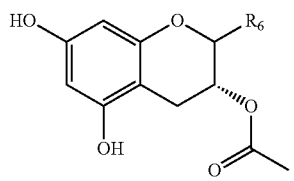
Formula (6)

wherein $R_5$ is OH, a group of Formula (7):

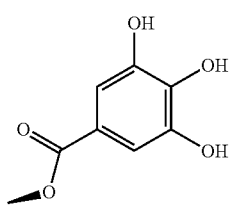
Formula (7)

or a group of Formula (8):

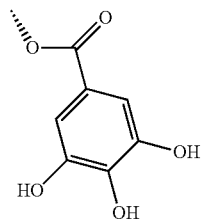
Formula (8)

wherein $R_6$ is a group of Formula (9):

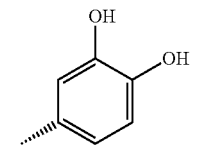
Formula (9)

or a group of Formula (10):

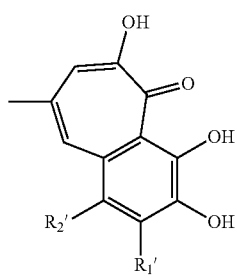
Formula (10)

wherein $R_1'$ is the same group as $R_1$ above and $R_2'$ is a group of Formula (11):

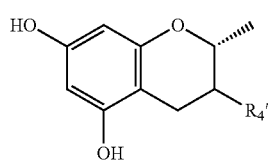
Formula (11)

wherein $R_4'$ is the same group as $R_4$ above, excluding epitheaflagallin, epitheaflagallin-3-O-gallate, theaflavin, theaflavin-3-O-gallate, theaflavin-3'-O-gallate, and theaflavin-3,3'-O-digallate.

2. The method of claim 1, wherein $R_1$ is H.

3. The method of claim 1, wherein the compound is a compound of:

Formula (13)
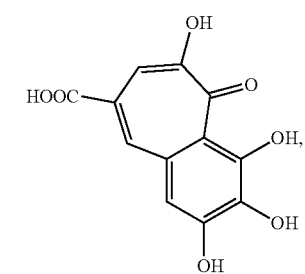
Formula (15)
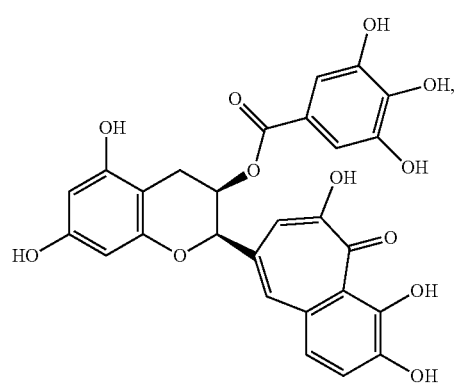
Formula (16)
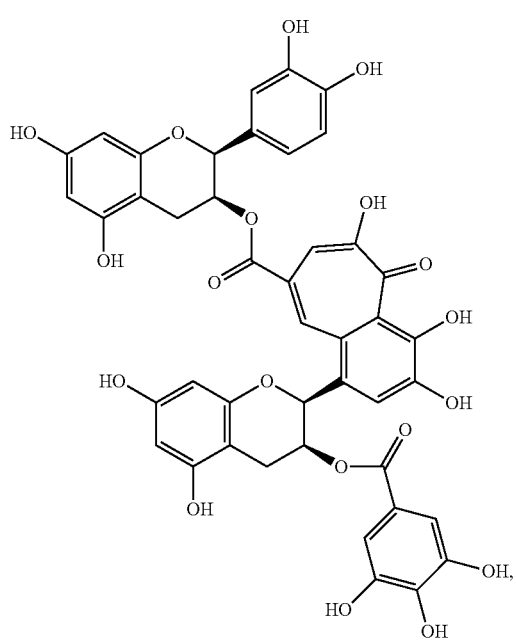
Formula (17)
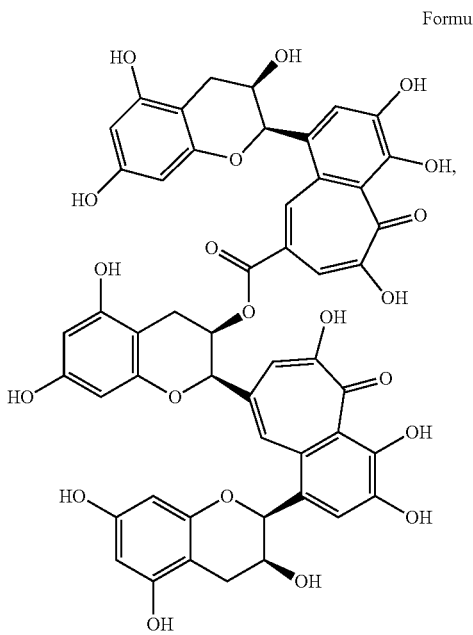
Formula (18)
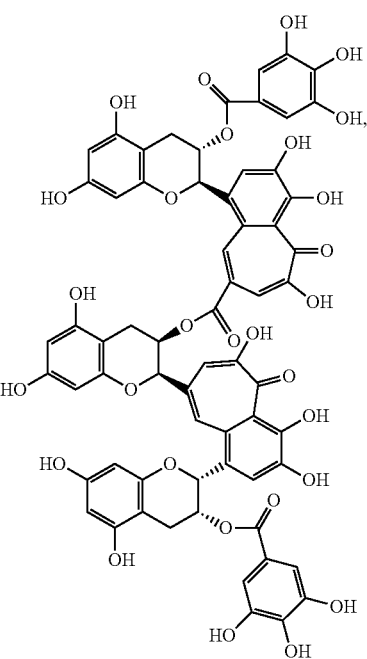

Formula (19)

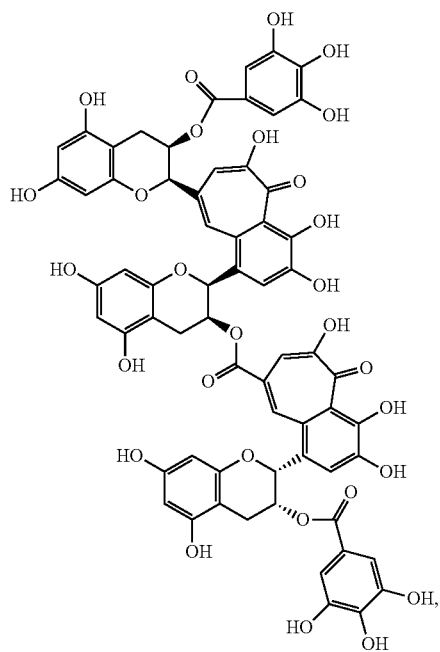

Formula (20)

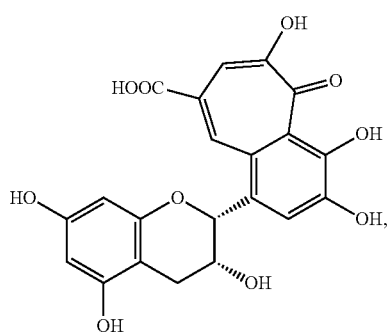

Formula (22)

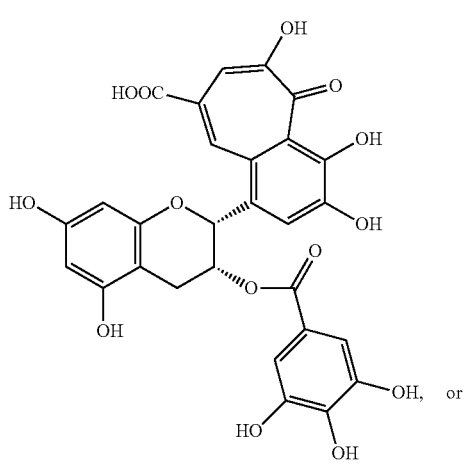
or

Formula (23)

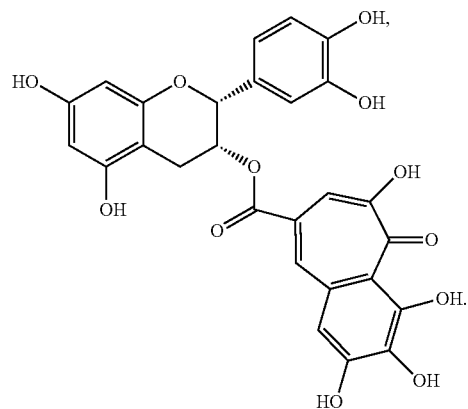

4. The method of claim 1, wherein the compound of Formula (1) is contained in a composition.

5. The method of claim 1, wherein the compound of Formula (1) is contained in a food or a beverage.

6. The method of claim 1, wherein the compound of Formula (1) is contained in a tea beverage, a soft drink, or a health food.

7. A method of inhibiting alpha-glucosidase activity comprising: administering one or more compounds of Formula (1) to a subject in need thereof, wherein the compounds of Formula (1) are selected from:

Formula (1)

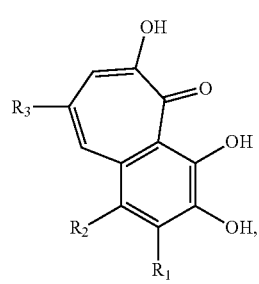

wherein $R_1$ is H or OH;

$R_2$ is H or a group of Formula (2):

Formula (2)

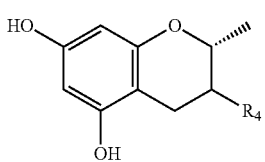

wherein $R_4$ is OH, a group of Formula (3):

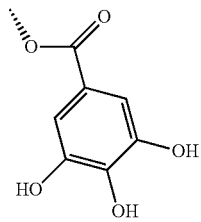

Formula (3)

or a group of Formula (4):

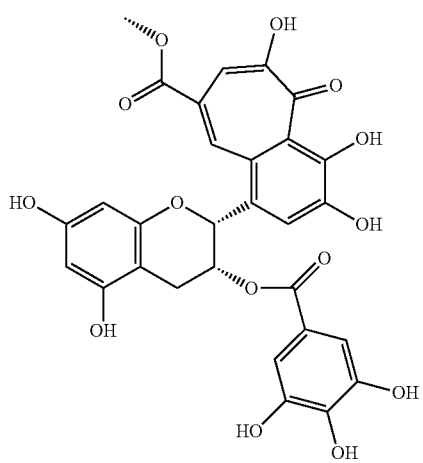

Formula (4)

$R_3$ is COOH, a group of Formula (5):

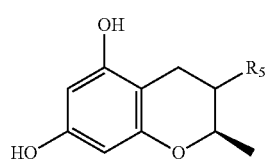

Formula (5)

or a group of Formula (6):

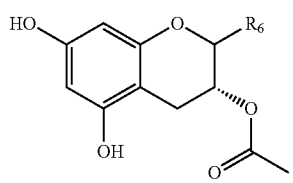

Formula (6)

wherein $R_5$ is OH, a group of Formula (7):

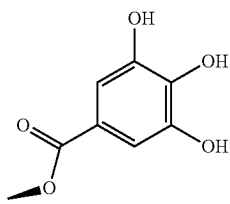

Formula (7)

or a group of Formula (8):

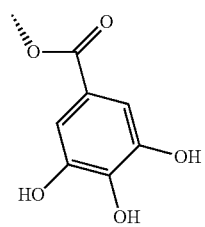

Formula (8)

wherein $R_6$ is a group of Formula (9):

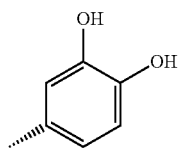

Formula (9)

or a group of Formula (10):

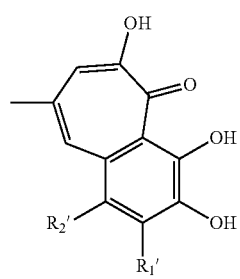

Formula (10)

wherein $R_1'$ is the same group as $R_1$ above and $R_2'$ is a group of Formula (11):

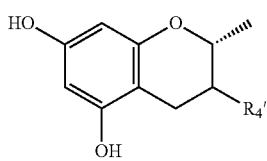

Formula (11)

wherein $R_4'$ is the same group as $R_4$ above,
excluding epitheaflagallin, epitheaflagallin-3-O-gallate, theaflavin, theaflavin-3-O-gallate, theaflavin-3'-O-gallate, and theaflavin-3,3'-O-digallate.

8. The method of claim 7, wherein $R_1$ is H.
9. The method of claim 7, wherein the compound is a compound of
Formula (13)
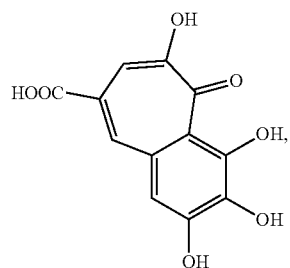
Formula (15)
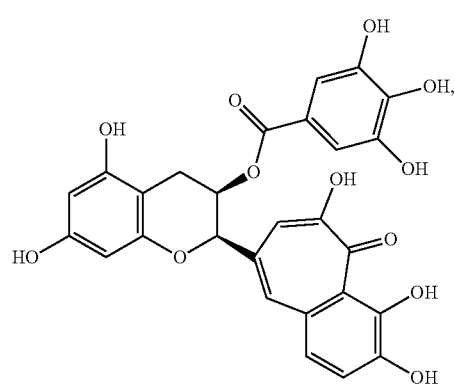
Formula (16)
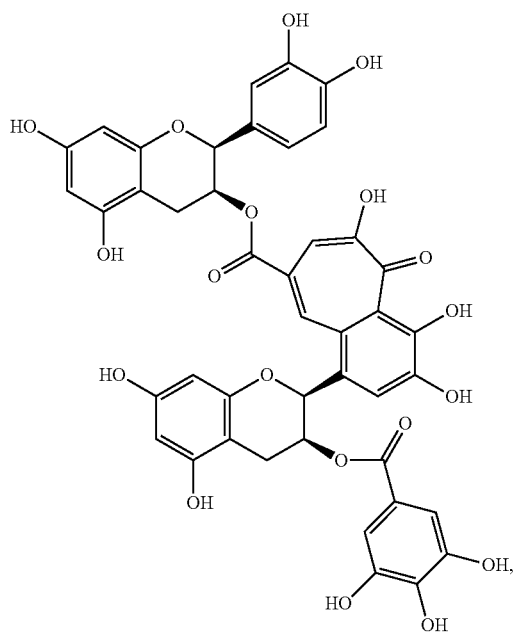
Formula (17)
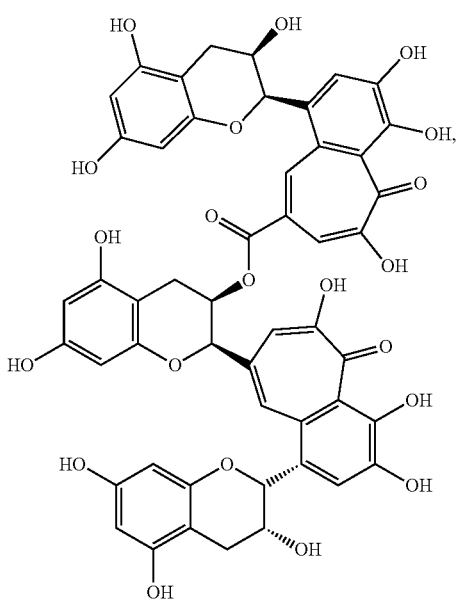
Formula (18)
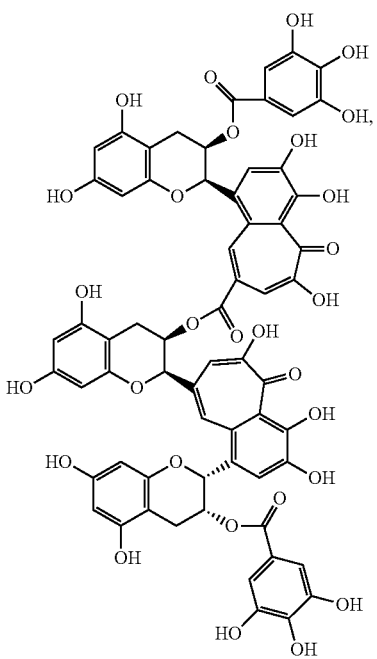

Formula (19)
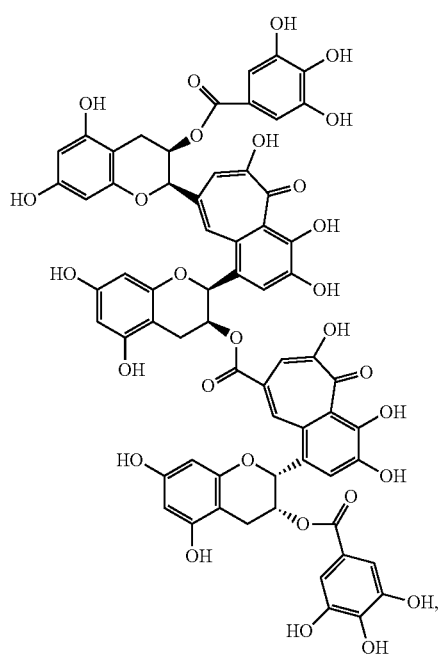
Formula (20)
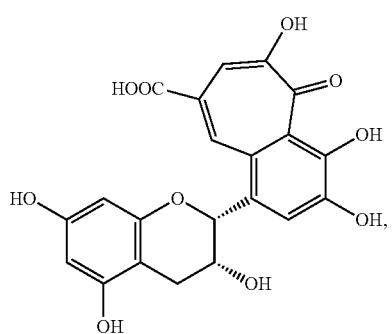
Formula (22)
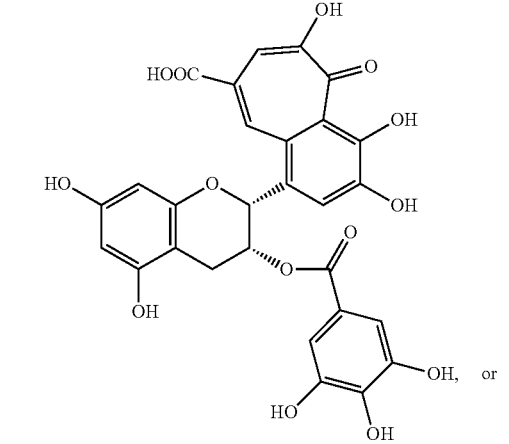
Formula (23)
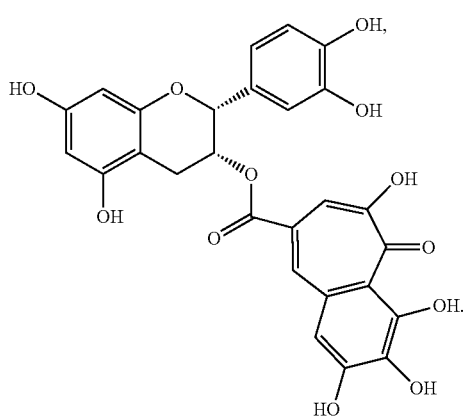
10. The method of claim 7, wherein the compound of Formula (1) is contained in a composition.
11. The method of claim 7, wherein the compound of Formula (1) is contained in a food or a beverage.
12. The method of claim 7, wherein the compound of Formula (1) is contained in a tea beverage, a soft drink, or a health food.
* * * * *